US012121637B2

(12) United States Patent
Gibson et al.

(10) Patent No.: US 12,121,637 B2
(45) Date of Patent: Oct. 22, 2024

(54) METHOD OF ATOMIZING A FLUID COMPOSITION

(71) Applicant: The Procter & Gamble Company, Cincinnati, OH (US)

(72) Inventors: Bruce David Gibson, Lexington, KY (US); Stephan Gary Bush, Liberty Township, OH (US); Chisomaga Ugochi Nwachukwu, Cincinnati, OH (US); Judith Ann Hollingshead, Batavia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 827 days.

(21) Appl. No.: 16/924,270

(22) Filed: Jul. 9, 2020

(65) Prior Publication Data

US 2021/0015958 A1 Jan. 21, 2021

Related U.S. Application Data

(60) Provisional application No. 62/875,098, filed on Jul. 17, 2019.

(51) Int. Cl.

| | |
|---|---|
| ***A61L 9/14*** | (2006.01) |
| ***A61L 9/03*** | (2006.01) |
| ***B01L 3/00*** | (2006.01) |

(52) U.S. Cl.

CPC .................. *A61L 9/14* (2013.01); *A61L 9/03* (2013.01); *B01L 3/502738* (2013.01); *A61L 2209/135* (2013.01)

(58) Field of Classification Search

CPC ........ A61L 9/14; A61L 9/03; A61L 2209/135; B10L 3/502738

(Continued)

(56) References Cited

U.S. PATENT DOCUMENTS 5,418,558 A * 5/1995 Hock .................. B41J 2/04513 347/14
5,682,183 A * 10/1997 Wade .................. B41J 2/04506 347/7

(Continued)

FOREIGN PATENT DOCUMENTS

CN 104661689 A 5/2015
CN 106456821 A 2/2017

(Continued)

OTHER PUBLICATIONS

JP2021511991 (Year: 2023).*

(Continued)

*Primary Examiner* — Nathaniel E Wiehe
*Assistant Examiner* — Frederick F Calvetti
(74) *Attorney, Agent, or Firm* — Carolyn S. Powell; Abbey A. Lopez

(57) ABSTRACT

A method of atomizing a fluid composition is provided that includes dynamically measuring the minimum-required actuation energy for the fluid composition. The method includes the steps of: connecting a microfluidic cartridge with a housing of a microfluidic device, the microfluidic cartridge comprising a reservoir containing the fluid composition and a microfluidic die in fluid communication with the reservoir; the microfluidic device comprising a controller; measuring the minimum-required actuation energy for the fluid composition at a first time; atomizing the fluid composition in a first atomization period; measuring the minimum-required actuation energy for a fluid composition at a second time that is after the first time; and atomizing the fluid composition in a second atomization period.

11 Claims, 11 Drawing Sheets

(58) Field of Classification Search
USPC .......................................................... 392/386
See application file for complete search history.

(56) References Cited

U.S. PATENT DOCUMENTS

| | | | | | |
|---|---|---|---|---|---|
| 5,699,090 | A | * | 12/1997 | Wade | B41J 2/04563 347/7 |
| 6,302,507 | B1 | | 10/2001 | Prakash | |
| 6,354,687 | B1 | * | 3/2002 | Su | B41J 2/04591 347/19 |
| 8,338,346 | B2 | * | 12/2012 | Diersing | A61L 9/01 512/26 |
| 9,278,150 | B2 | | 3/2016 | Gruenbacher | |
| 9,636,430 | B2 | * | 5/2017 | Gruenbacher | B05B 7/0012 |
| 10,076,585 | B2 | | 9/2018 | Gruenbacher | |
| 2002/0024547 | A1 | * | 2/2002 | Miyakoshi | B41J 2/04553 347/14 |
| 2010/0165029 | A1 | * | 7/2010 | Gibson | B41J 2/04528 347/14 |
| 2013/0147868 | A1 | * | 6/2013 | Oikawa | B41J 2/04563 347/10 |
| 2013/0309102 | A1 | * | 11/2013 | Gruenbacher | A61L 9/145 417/54 |
| 2014/0078229 | A1 | * | 3/2014 | Jackson | C09D 11/40 347/95 |
| 2015/0265739 | A1 | | 9/2015 | Gruenbacher | |
| 2015/0367356 | A1 | * | 12/2015 | Gruenbacher | B41J 2/17509 239/135 |
| 2018/0140733 | A1 | * | 5/2018 | Webb | A61L 9/03 |
| 2018/0290156 | A1 | | 10/2018 | Gruenbacher et al. | |
| 2019/0126616 | A1 | | 5/2019 | Canto Estany | |
| 2020/0138996 | A1 | * | 5/2020 | Chen | A61L 9/03 |
| 2020/0276813 | A1 | | 9/2020 | Doumaux | |

FOREIGN PATENT DOCUMENTS

| | | | | |
|---|---|---|---|---|
| EP | 0623469 | A3 | | 8/1995 |
| JP | H071736 | A | | 1/1995 |
| JP | H071736 | | * | 10/2004 |
| JP | 2017523823 | | * | 8/2017 |
| JP | 2017523823 | A | | 8/2017 |
| WO | WO2018017054 | | * | 1/2018 |
| WO | WO2019094009 | | * | 5/2019 |

OTHER PUBLICATIONS

JP2017523823 (Year: 2023).*
WO2019/094009 (Year: 2024).*
WO2020/208484 (Year: 2024).*
WO2016/205029 (Year: 2024).*
CN105042654 (Year: 2024).*
CN203431951 (Year: 2024).*
CN204987134 (Year: 2024).*
International Search Report and Written Opinion; Application Ser. No. PCT/US2020/070273; dated Oct. 14, 2020, 13 pages.

* cited by examiner

METHOD OF ATOMIZING A FLUID COMPOSITION

FIELD

The present disclosure is directed to a method of atomizing a fluid composition, and more particularly, to a method of atomizing a fluid composition from a microfluidic die by dynamically adjusting the firing energy based on measurement of the minimum-required actuation energy.

BACKGROUND

Recent attempts have been made to deliver fluid compositions, such as freshening compositions comprising perfume mixtures, into the air using microfluidic devices. Such microfluidic devices may include a microfluidic die having a plurality of nozzles for jetting the fluid composition. Over time, the dispensing from the microfluidic die can change. This may be due to one or more factors, including buildup of components from the fluid composition on the microfluidic die surface in or around the nozzles, heat-generated reactants in the fluid composition that deposit on the microfluidic die surfaces, and changes brought about in the fluid composition due to age or environmental factors. As such, there remains a need for a method of atomizing a fluid composition from a microfluidic die that improves the consistency of the dispensing of the fluid composition over time.

SUMMARY

"Combinations:"

A. A method of atomizing a fluid composition, the method comprising the steps of:

connecting a microfluidic cartridge with a housing of a microfluidic device, the microfluidic cartridge comprising a reservoir containing the fluid composition and a microfluidic die in fluid communication with the reservoir; the microfluidic device comprising a controller;

measuring the minimum-required actuation energy for the fluid composition at a first time;

atomizing the fluid composition in a first atomization period;

measuring the minimum-required actuation energy for a fluid composition at a second time that is after the first time; and atomizing the fluid composition in a second atomization period.

B. The method of Paragraph A, further comprising the step of repeating the measurement of minimum-required actuation energy after subsequent atomization periods.

C. The method of Paragraph A or Paragraph B, wherein the fluid composition comprises a perfume mixture.

D. The method of any of Paragraphs A through C, wherein the fluid composition comprises at least ten components, preferably at least 20 components, more preferably at least 30 components, and most preferably at least 40 components.

E. The method of Paragraph D, wherein the ten or more components have a range of vapor pressures encompassing $1.3\times10^{-7}$ Pa to 2000 Pa at 20° C. and having a ratio of highest to lowest vapor pressure of at least $1.5\times10^{10}$.

F. The method of any of Paragraphs A through E, wherein the fluid composition comprises one or more reactive components that are capable of forming solids.

G. The method of any of Paragraphs A through F, wherein the fluid composition comprises three or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

H. A method of atomizing a fluid composition from a microfluidic die, the microfluidic die comprising a substrate and a plurality of nozzles, a thermal actuator associated with each nozzle, and wherein the actuator is responsive to a pulse for energizing the fluid composition and jetting the fluid composition through the nozzle, and a thermal sensor for measuring a temperature of the substrate of the microfluidic die, the method comprising the steps of:

determining a firing energy to drive the thermal actuators to jet the fluid composition at a first time, the step of determining the firing energy comprising the steps of:

a) heating the microfluidic die to a predetermined temperature by driving the actuators during a first mode with pulses having a pulse width and a starting frequency that are too short to cause bubble nucleation;
b) driving the actuators during a second mode with respective pulses having decremented pulse widths and frequencies having incremented frequencies, starting at a pulse width known to cause droplet ejection and ending at a pulse width too short to cause droplet ejection;
c) processing a temperature change of the microfluidic die during each interval to determine a minimum-required actuation energy that caused a predetermined temperature change;
d) applying a factor to the determined minimum-required actuation energy to determine a firing energy; and using the firing energy to drive the thermal actuators to jet the fluid composition;

repeating the step of measuring the firing energy to determine a second firing energy at a second time after the first time; and using the second firing energy to drive the thermal actuators to jet a fluid composition.

I. The method of Paragraph H further comprising the step of repeating the measurement of minimum-required actuation energy after subsequent atomization periods.

J. The method of Paragraph H or Paragraph I, wherein the fluid composition comprises a perfume mixture.

K. The method of any of Paragraphs H through J, wherein the fluid composition comprises at least ten components, preferably at least 20 components, more preferably at least 30 components, and most preferably at least 40 components.

L. The method of Paragraph K, wherein the ten or more components have a range of vapor pressures encompassing $1.3\times10^{-7}$ Pa to 2000 Pa at 20° C. and having a ratio of highest to lowest vapor pressure of at least $1.5\times10^{10}$.

M. The method of any of Paragraphs H through L, wherein the fluid composition comprises three or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

N. The method of any of Paragraphs H through M, wherein the fluid composition comprises one or more reactive components that form solids.

O. A method of atomizing a fluid composition from a microfluidic die, the microfluidic die comprising a plurality of nozzles, an actuator associated with each nozzle, and wherein the actuator is responsive to a pulse for energizing the fluid composition and jetting the fluid composition through the nozzle, a means of heating the microfluidic die substrate, and a thermal sensor for measuring microfluidic die substrate temperature, comprising:

measuring a firing energy to drive the actuators to jet the fluid composition at a first time, the step of measuring the firing energy comprising the steps of:

a) heating the microfluidic die substrate to a predetermined temperature during a first mode;

b) driving the actuators during a second mode with respective pulses having decremented actuation energy and maintaining a constant power applied to the microfluidic die substrate, starting at an actuation energy known to cause drop ejection and ending at an actuation energy too small to cause drop ejection;

c) processing a temperature change of the microfluidic die during each interval to determine a minimum-required actuation energy that caused a predetermined temperature change;

d) applying a factor to the determined minimum-required actuation energy to determine a firing energy; and using the firing energy to drive the actuators to jet the fluid composition;

repeating the step of measuring the minimum-required actuation energy to determine a second firing energy at a second time after the first time; and using the second firing energy to drive the actuators to jet a fluid composition.

P. The method of Paragraph O, further comprising the step of repeating the measurement of minimum-required actuation energy after subsequent atomization periods.

Q. The method of Paragraph O or Paragraph P, wherein the fluid composition comprises a perfume mixture.

R. The method of any of Paragraphs O through Q, wherein the fluid composition comprises at least ten components, preferably at least 20 components, more preferably at least 30 components, and most preferably at least 40 components.

S. The method of Paragraph R, wherein the ten or more components have a range of vapor pressures encompassing $1.3\times10^{-7}$ Pa to 2000 Pa at 20° C. and having a ratio of highest to lowest vapor pressure of at least $1.5\times10^{10}$.

T. The method of any of Paragraphs O through S, wherein the fluid composition comprises three or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

DETAILED DESCRIPTION

Figure 1:
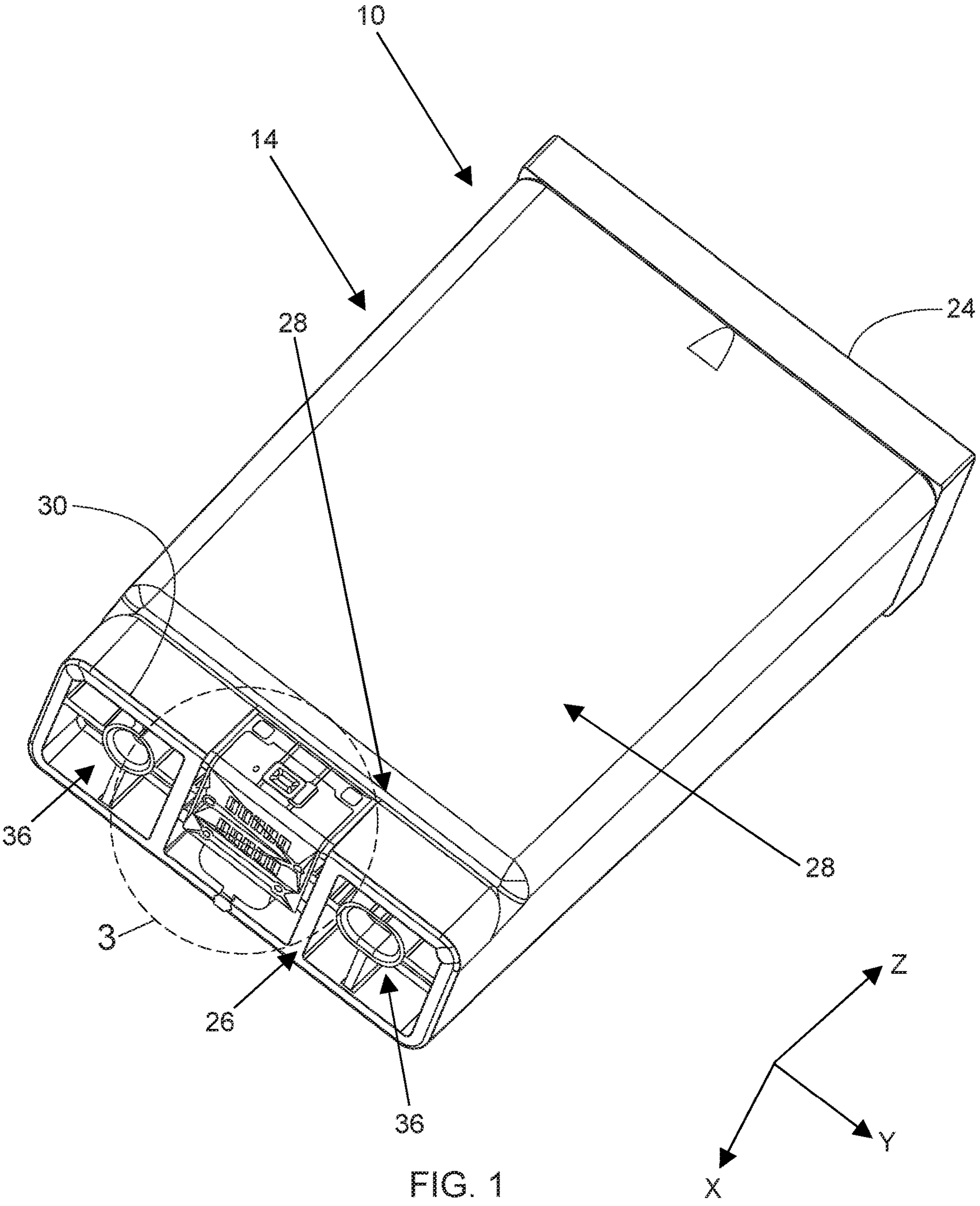
FIG. 1 is a perspective view of a microfluidic cartridge with an electric circuit and microfluidic die.

While the below description describes a fluid composition, a microfluidic delivery device and a method of atomizing a fluid composition, both having various components, it is to be understood that the fluid composition, microfluidic delivery device, and method of atomizing a fluid composition are not limited to the construction and arrangement set forth in the following description or illustrated in the drawings.

The present disclosure is directed to a method of atomizing a fluid composition from a microfluidic die. The method of atomizing a fluid composition of the present invention includes dynamically measuring the minimum-required actuation energy and adjusting the actuation energy applied by the microfluidic die over time in order to improve the consistency of atomized droplet flow rate, droplet size, etc. over the life of a cartridge.

A microfluidic delivery device may include a housing electrically connectable with a power source, a cartridge releasably connectable with the housing. The cartridge has a reservoir for containing a fluid composition and a microfluidic die in fluid communication with the reservoir.

Microfluidic Device

Figure 2:
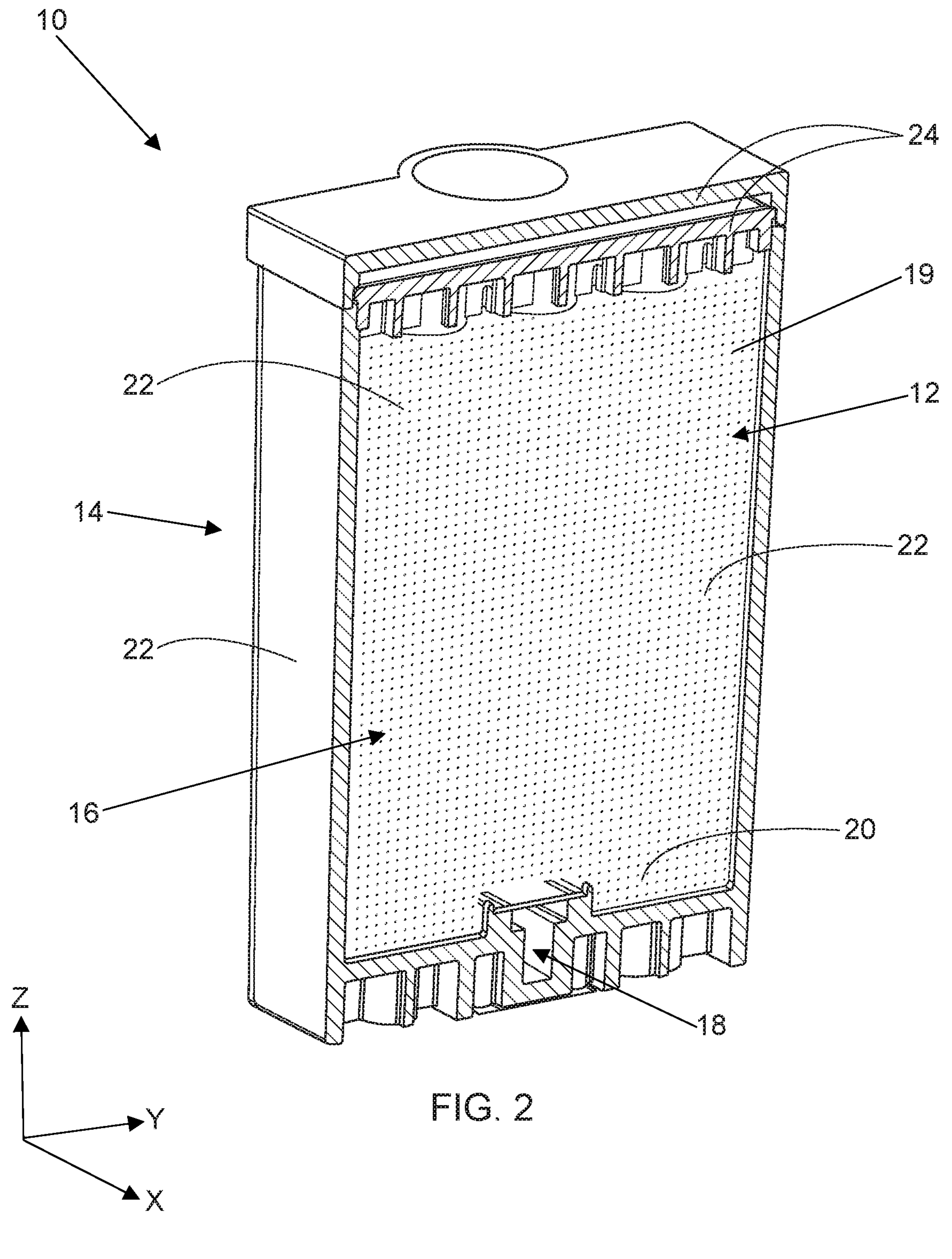
FIG. 2 is a sectional view of a microfluidic cartridge.
Figure 3:
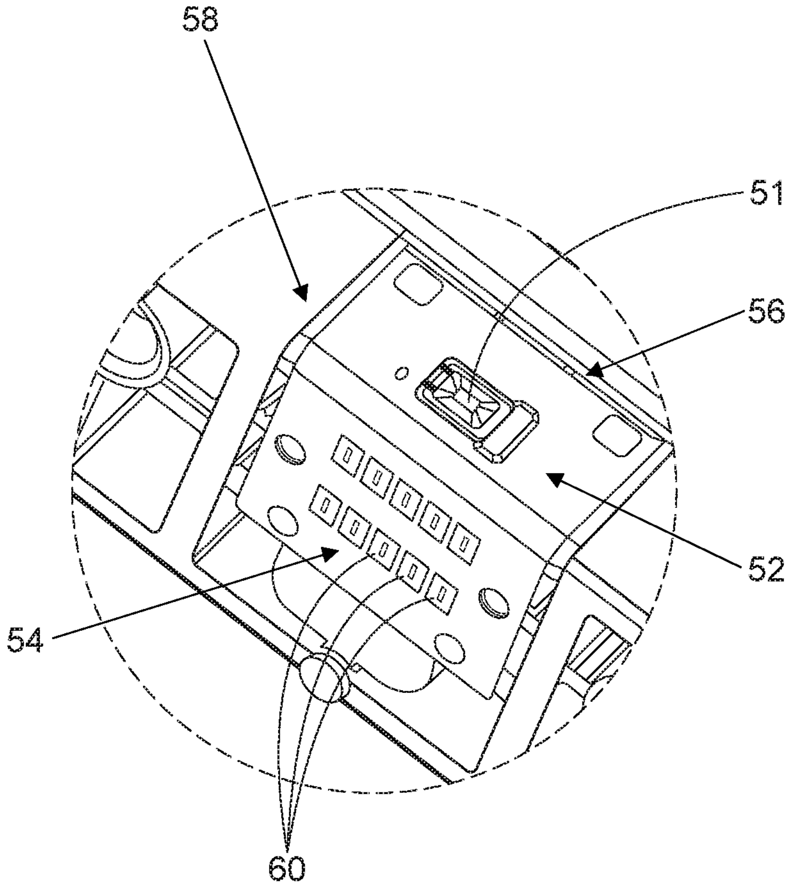
FIG. 3 is an exploded view of an electric circuit and microfluidic die on a microfluidic cartridge.

With reference to FIGS. 1-3, a microfluidic cartridge 10 comprises an interior 12 and an exterior 14. The interior 12 of the microfluidic cartridge 10 comprises a reservoir 16 and one or more fluid channels 18 that are in fluid communication with the microfluidic die 51. The reservoir 16 may be formed from a base wall 20 or a plurality of surfaces forming a base wall 20 and one or more side walls 22. The reservoir 16 may be enclosed by a lid 24 of the microfluidic cartridge 10. The fluid channel 18 extends from reservoir 16 to the exterior 14 of the microfluidic cartridge 10 at the fluid opening. The reservoir may include an air vent. The lid 24 may be integral with the reservoir 16 or may be constructed as a separate element that is connected with the reservoir 16.

The reservoir 16 of the microfluidic cartridge 10 may contain from about 5 mL to about 50 mL of fluid composition, alternatively from about 10 mL to about 30 mL of fluid composition, alternatively from about 15 mL to about 20 mL of fluid composition. The reservoir 16 can be made of any suitable material for containing a fluid composition. Suitable materials for the containers include, but are not limited to, plastic, metal, ceramic, composite, and the like. A microfluidic cartridge may be configured to have multiple reservoirs, each containing the same or a different composition. The microfluidic delivery device may utilize one or more microfluidic cartridges, each containing a separate reservoir.

The reservoir 16 may also contain a porous material 19 such as a sponge that creates a back pressure to prevent the fluid composition from leaking from the microfluidic die when the microfluidic die is not in operation. The fluid composition may travel through the porous material and to the microfluidic die through gravity force and/or capillary force acting on the fluid composition. The porous material may comprise a metal or fabric mesh, open-cell polymer foam, or fibrous polyethylene terephthalate, polypropylene, or bi-components of fibers or porous wick, that contain multiple interconnected open cells that form fluid passages. The sponge may include polyurethane foam.

With reference to FIG. 1, the exterior 14 of the microfluidic cartridge 10 is made up of two, three, or more faces. Each face is bounded by one or more edges. Two faces are connected along an edge. Each face may be flat, substantially flat, or contoured in various ways. The faces may connect to form various shapes, such as a cube, cylinder, cone, tetrahedron, triangular prism, cuboid, etc. The microfluidic cartridge may be comprised of various materials, including plastic, metal, glass, ceramic, wood, composite, and combinations thereof. Different elements of the microfluidic cartridge may be comprised of the same or different materials.

The microfluidic cartridge 10 may comprise at least a first face 26 and a second face 28 joined along an edge 30. For example, the first face 26 may be a bottom face and the second face 28 may be a side face.

In a microfluidic cartridge 10 that is substantially cube-shaped, the microfluidic cartridge 10 may include a top face, a bottom face that opposes the top face, and four side faces extending between the top and bottom faces. Each joining face may be connected along an edge. In a cylindrical-shaped microfluidic cartridge, for example, the microfluidic cartridge may include a top face, a bottom face opposing the top face, and a single curved side face extending between the top and bottom faces.

With reference to FIGS. 1-3, the fluid channel 18 of the microfluidic cartridge 10 may extend to a fluid opening that may be disposed in the second face 28 of the microfluidic cartridge 10. The microfluidic cartridge 10 may include a microfluidic die 51 disposed on the second face 28. The fluid channel 18 may open up to the microfluidic die 51 such that the fluid channel 18 is in fluid communication with the microfluidic die 51.

The primary components of a microfluidic die are a semiconductor substrate, a flow feature layer, and a nozzle plate layer. The flow feature layer and the nozzle plate layer may be formed from two separate layers or one continuous layer. The semiconductor substrate is preferably made of silicon and contains various passivation layers, conductive metal layers, resistive layers, insulative layers and protective layers deposited on a device surface thereof. Fluid ejection actuators in the semiconductor substrate generate rapid pressure impulses to eject the fluid composition from the nozzles. The rapid pressure impulses may be generated by piezoelectric device that vibrates at a high frequency (e.g., micro mechanical actuation) or by a heater resistor that cause volatilization of a portion of a fluid composition within the fluid composition through rapid heating cycles (e.g., micro thermal nucleation). For thermal actuators, individual heater resistors are defined in the resistive layers and each heater resistor corresponds to a nozzle in the nozzle plate for heating and ejecting the fluid composition from the nozzle.

Figure 4:
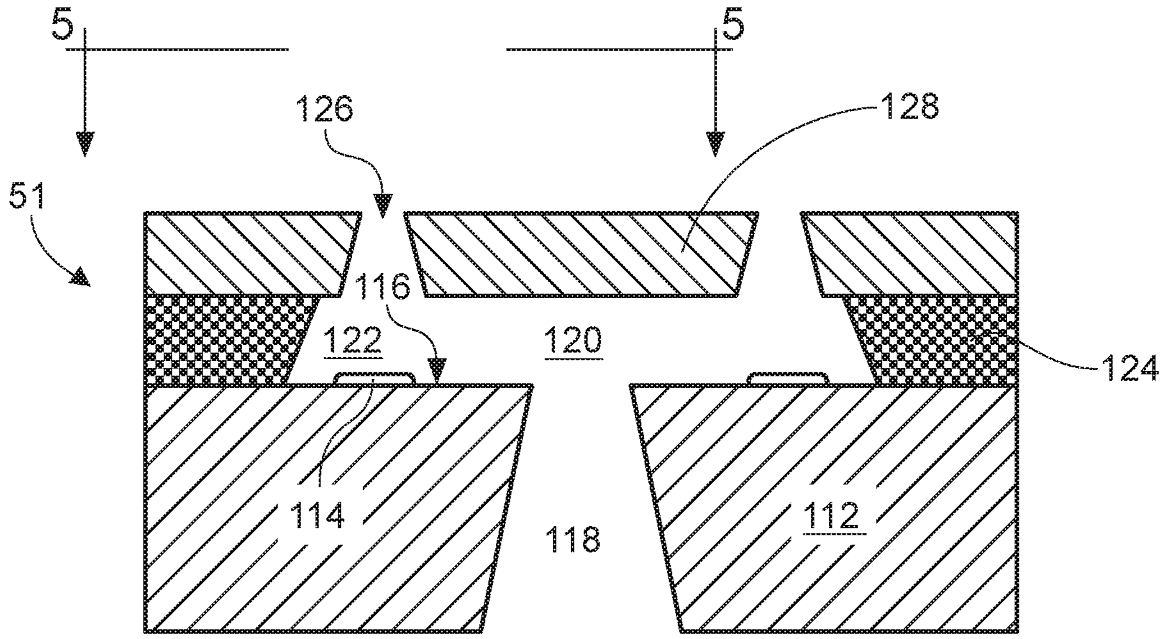
FIG. 4 is a sectional view of a microfluidic die.
Figure 5:
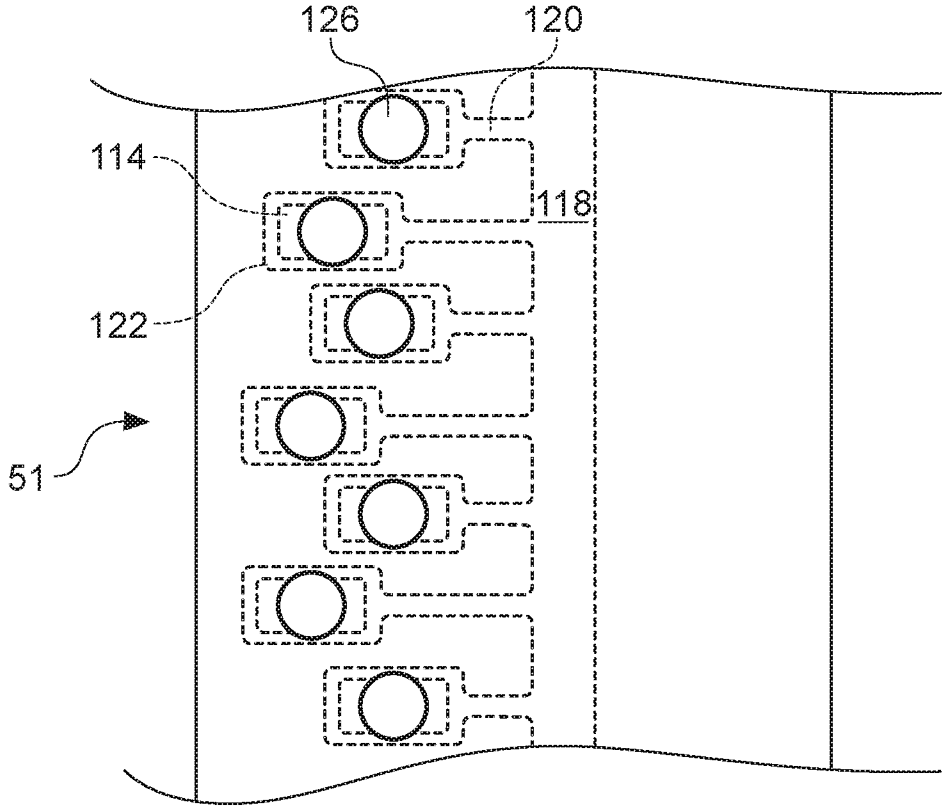
FIG. 5 is a plan view of a portion of a microfluidic die.

With reference to FIGS. 4 and 5, there is shown a simplified representation of a portion of a microfluidic die 51. The microfluidic die includes a semiconductor substrate 112 that may be a silicon semiconductor substrate 112 containing a plurality of fluid ejection actuators 114 such as piezoelectric devices or heater resistors formed on a device side 116 of the substrate 112 as shown in the simplified illustration of FIG. 5. In a microfluidic die having piezo actuators as the fluid ejection actuators 114, the piezo actuator may be disposed adjacent the nozzle such as shown in FIG. 5 or may be disposed away from the nozzles and still transmit the pressure pulse to the fluid composition to be ejected from the nozzles. Upon activation of fluid ejection actuators 114, fluid supplied through one or more fluid supply vias 118 in the semiconductor substrate 112 flows through a fluid supply channel 120 to a fluid chamber 122 in a thick film layer 124 where the fluid is caused to be ejected through nozzles 126 in a nozzle plate 128. Fluid ejection actuators are formed on the device side 116 of the semiconductor substrate 112 by well-known semiconductor manufacturing techniques. Thick film layer 124 and nozzle plate 128 may be separate layers or may be one continuous layer.

The nozzle plate 128 may include about 4-200 nozzles 126, or about 6-120 nozzles, or about 8-64 nozzles. Each nozzle 126 may deliver about 0.5 to about 35 picoliters, or about 1 to about 20 picoliters, or about 2 to about 10 picoliters of a fluid composition per electrical firing pulse. Individual nozzles 126 may have of a diameter typically about 0.0024 inches (5-50 microns). The flow rate of fluid composition released from the microfluidic die 51 could be in the range of about 5 to about 70 mg/hour or any other suitable rate or range.

With reference to FIGS. 1 and 3, the microfluidic cartridge 10 comprises an electric circuit 52. The electric circuit 52 may be in the form of a flexible circuit, semi-flexible circuit having rigid and flexible portions, and rigid circuit boards. The electric circuit 52 may include a first end portion 54, a second end portion 56, and a central portion 58 separating the first and second end portions 54 and 56, respectively. The first end portion 54 of the electric circuit 52 may include electrical contacts 60 for connecting with the electrical contacts of the housing of a microfluidic delivery device. The second end portion 56 of the electric circuit 52 may be in electrical communication with the microfluidic die 51.

In the case of a flexible or semi-flexible electric circuit 52, the electric circuit 52 may be disposed on and span two faces of the microfluidic cartridge 10. For example, with reference to FIGS. 1 and 3, for illustrative purposes only, the first end portion 54 of the electric circuit 52 may be disposed on the first face 26 of the microfluidic cartridge 10, the second end portion 56 of the electric circuit 52 may be disposed on the second face 28 of the microfluidic cartridge 10, and the central portion 58 of the electric circuit 52 may span the first and second faces 26 and 28, respectively, of the microfluidic cartridge 10.

In the case of a rigid electric circuit 52, the electric circuit 52 may be disposed on a single face of the microfluidic cartridge 52 such that the microfluidic die 51 and the electrical contacts 60 are disposed on the same face.

With reference to FIGS. 1 and 6-8, the microfluidic cartridge 10 may also comprise one or more cartridge connectors 36 to provide mechanical connection between the microfluidic cartridge 10 and the housing. A cartridge connector 36 on the microfluidic cartridge 10 may connect with or mate with a corresponding housing connector on the housing. For example, the cartridge connectors 36 may be configured as female connectors, such as openings that are configured to mate with one or more male connectors such as projections or guideposts, on the housing. Or, the cartridge connector 36 may be configured as a male connector may include one or more projections, such as guideposts, that are configured to mate with one or more female connectors such as openings on the housing. The mechanical connection between the microfluidic cartridge and the housing may help to properly align and secure the microfluidic cartridge in the housing to provide a robust electrical connection between the microfluidic cartridge and the housing.

Figure 6:
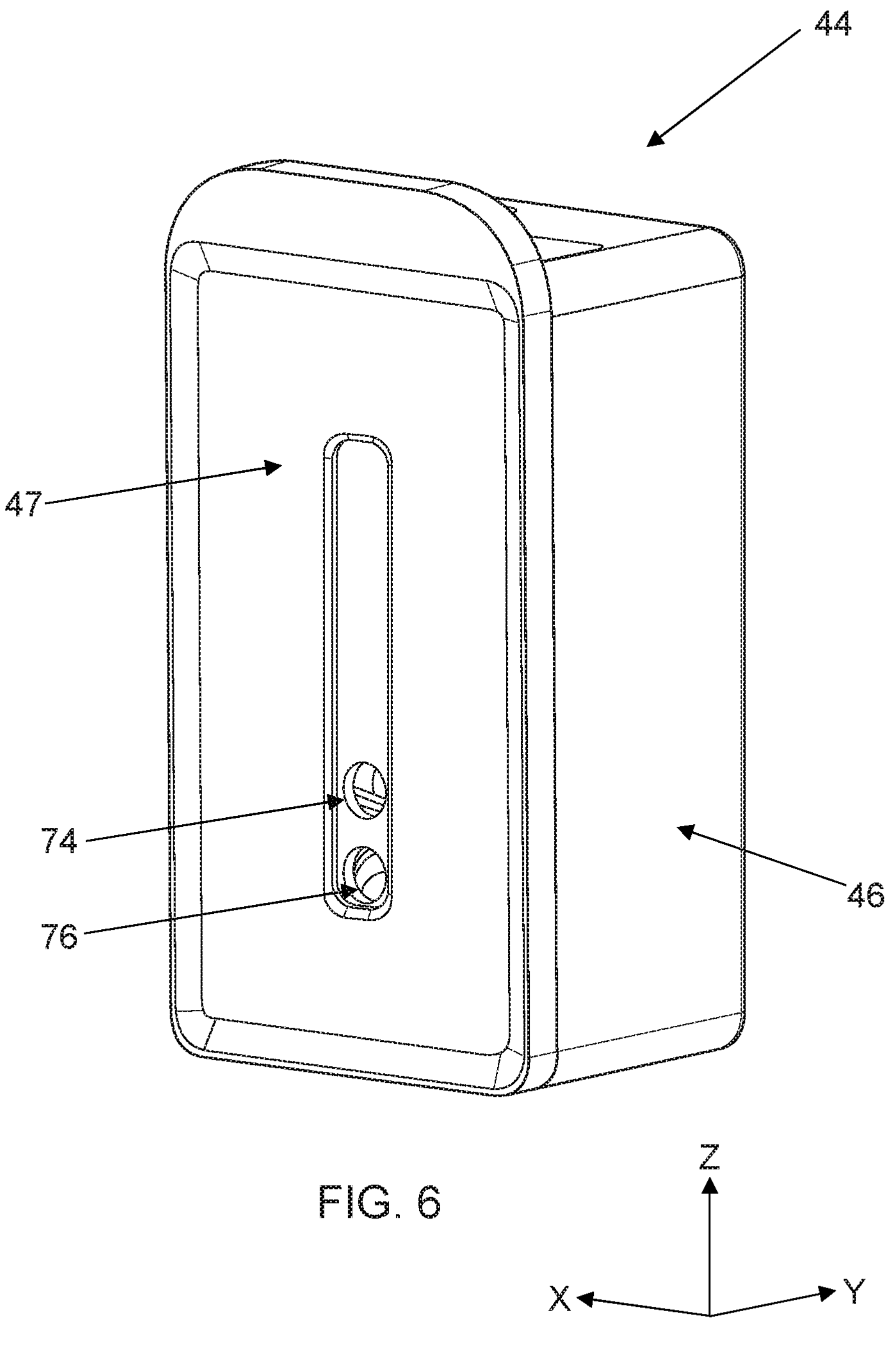
FIG. 6 is a perspective view of the front of a microfluidic delivery device.
Figure 7:
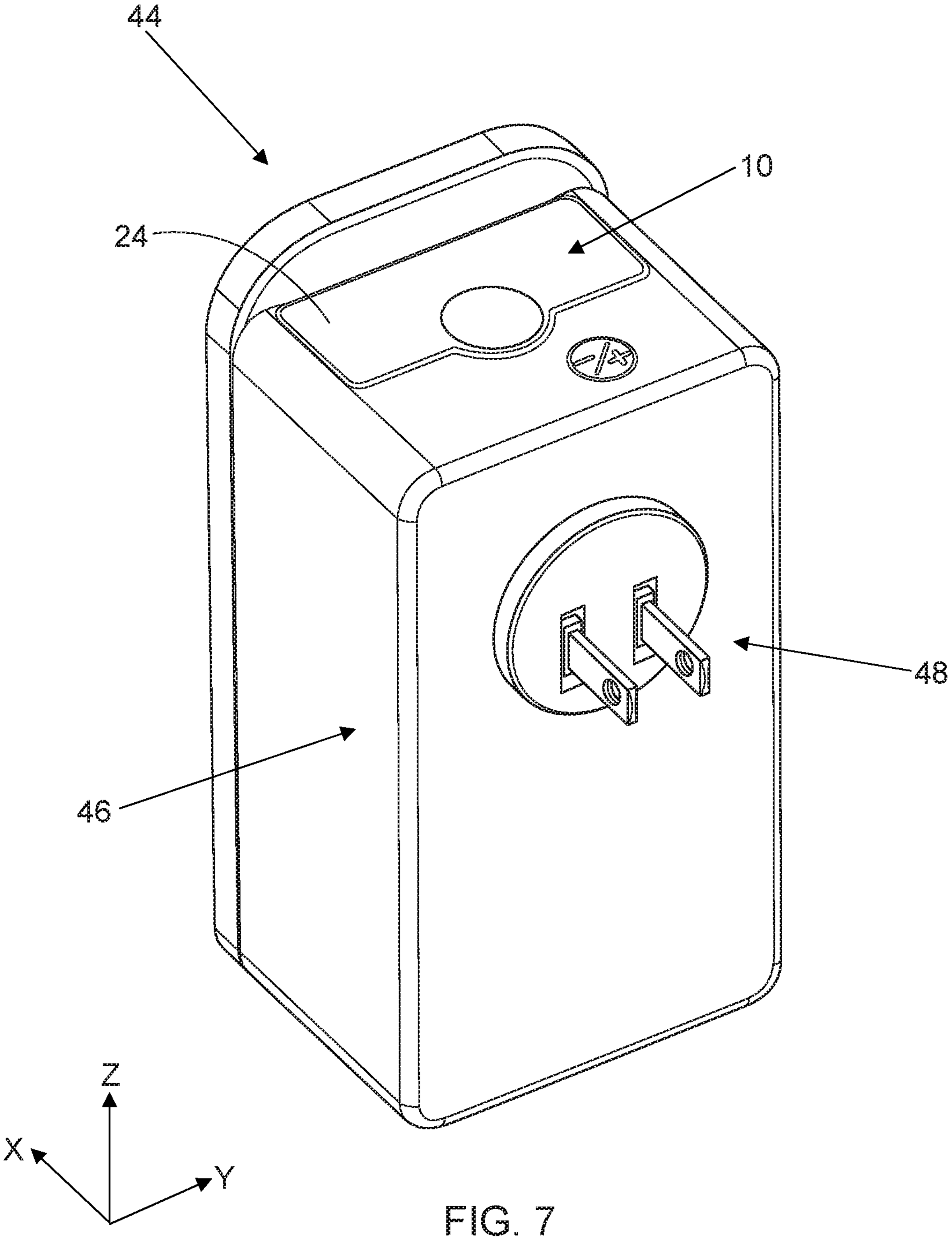
FIG. 7 is a perspective view of the back of a microfluidic delivery device.
Figure 8:
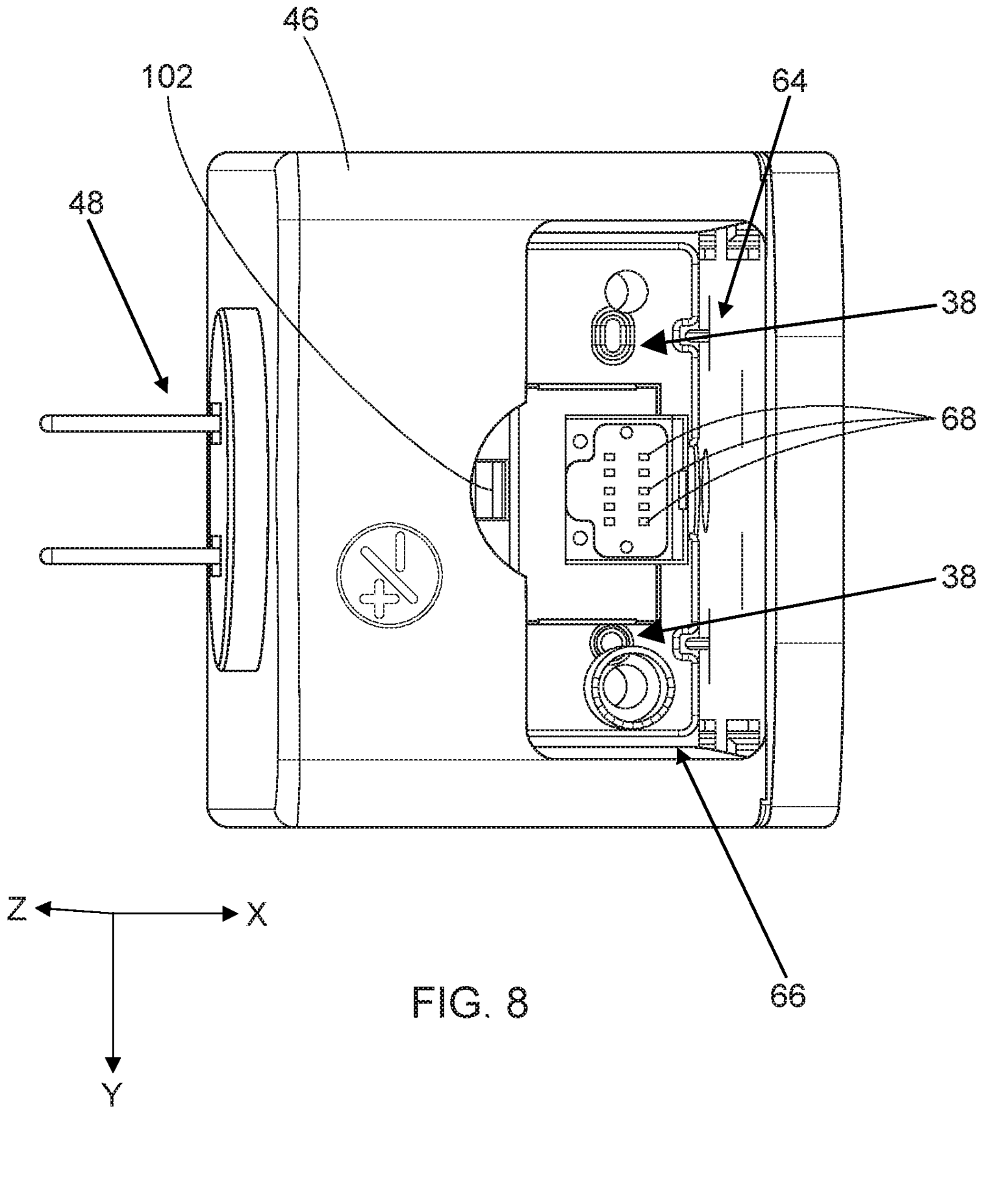
FIG. 8 is a top, plan view of a microfluidic delivery device.

With reference to FIGS. 6-8, a microfluidic cartridge 10 may be configured to be releasably connectable with a housing 46 of a microfluidic delivery device 44. The housing 46 may be connected with a power source 48. The housing 46 may include a receptacle 64 having an opening 66 for receiving the microfluidic cartridge 10. The receptacle 64 may receive a portion of the microfluidic cartridge 10 or the microfluidic cartridge 10 may be completely disposed within the receptacle 64. The receptacle 64 of the housing 46 may include electrical contacts 68 that are configured to electrically connect with the electrical contacts 60 of the microfluidic cartridge 10.

The microfluidic die 92 may be controlled and driven by an external microcontroller or microprocessor. The external microcontroller or microprocessor may be provided in the housing.

The receptacle 64 may include one or more housing connectors 38 configured to be received by the one or more cartridge connectors 36 of the microfluidic cartridge 10. The housing connectors 38 may be in the form of male connectors or female connectors. For example, if the cartridge connectors 36 are configured as female connectors, the housing connectors 38 may be configured as male connectors, or vice versa. The housing connectors 38 and cartridge connectors 36 may be sized and shaped to mate with each other for a sufficient mechanical and electrical connection to occur.

The housing 46 may include a faceplate 47 disposed on a front side of the housing 46. The housing 46 may also include a fluid outlet 74 for releasing the fluid composition from the microfluidic cartridge 10 into the air. The housing 46 may include an air outlet 76 for directing air toward the dispensed fluid composition upward and/or outward into the surrounding space. The fluid outlet 74 and the air outlet 76 may be disposed in the faceplate 47.

With reference to FIGS. 1 and 8, the cartridge connectors 36 and the housing connectors 38 may be used to align, secure, and limit movement of the microfluidic cartridge 10 relative to the housing of a microfluidic delivery device 44 to establish a strong electrical connection between the microfluidic cartridge 10 and the housing. The cartridge connectors 36 and the housing connectors 38 may be designed to provide either macro or micro alignment of the microfluidic cartridge 10. Mating the cartridge connectors 36 with the housing connectors 38 may prevent movement of the microfluidic cartridge 10 relative to the housing 46 of the microfluidic delivery device 44 in the X and Y-directions.

With reference to FIG. 8, the microfluidic cartridge 10 may be spring-loaded with the housing 46 in order to provide a robust electrical connection between the microfluidic cartridge 10. The microfluidic cartridge 10 may have a release button to release the microfluidic cartridge 10 from the housing 46. Or, the microfluidic cartridge 10 may be pushed toward the housing 46 to engage and/or disengage the microfluidic cartridge 10 from the housing 46. The microfluidic cartridge 10 may engage with a fastener 102 or clip to connect the microfluidic cartridge 10 into the housing 46.

The receptacle 64 may include one or more guiderails for directing the microfluidic cartridge 10 into the receptacle 64.

The microfluidic delivery device may be configured to be compact and easily portable. In such case, the microfluidic delivery device may be battery operated. The microfluidic delivery device may be capable for use with electrical sources as 9-volt batteries, conventional dry cells such as "A", "AA", "AAA", "C", and "D" cells, button cells, watch batteries, solar cells, as well as rechargeable batteries with recharging base.

The microfluidic delivery device may include a fan for generating air flow to assist with delivering the fluid composition into the air. Any fan may be used that provides the desired air flow velocity, size, and power requirements for the microfluidic delivery device. The fan may be used to push the fluid composition further into the air and/or may be used to direct the fluid composition in a different direction than the fluid composition is dispensed from the microfluidic die. The fan may be disposed in the interior of the housing or at least partially in the interior of the housing, or at the exterior of the housing. The fan may also be used to direct air over the microfluidic die 51 to minimize the amount of fluid composition that is deposited back onto the microfluidic die 51.

Method of Atomizing a Freshening Composition A method of atomizing a fluid composition may include applying energy to the fluid composition through the actuators of the microfluidic die and atomizing the composition from nozzles. The firing energy or minimum-required actuation energy may be periodically assessed to determine the optimal energy to apply to the actuators.

The fluid composition may be dispensed from the microfluidic die in a direction that is from 0 degrees to 90 degrees from the direction of action of gravity. Heating the fluid composition may be accomplished with a thermally-activated microfluidic die.

The microfluidic delivery device and method of delivering a freshening composition may be used to deliver a fluid composition into the air. The microfluidic delivery device may also be used to deliver a fluid composition into the air for ultimate deposition on one or more surfaces in a space. Exemplary surfaces include hard surfaces such as counters, appliances, floors, and the like. Exemplary surfaces also include carpets, furniture, clothing, bedding, linens, curtains, and the like. The microfluidic delivery device may be used in homes, offices, businesses, open spaces, cars, temporary spaces, and the like. The microfluidic delivery device may be used for freshening, malodor removal, insect repellant, and the like.

Minimum-Required Actuation Energy

The minimum-required actuation energy for a microfluidic die is the minimum energy that is required to cause a droplet to be ejected from a nozzle of the microfluidic die. Operating at an energy below the minimum-required actuation energy will not result droplet ejection from the nozzle, while operating above the minimum-required actuation energy will result in droplet formation and ejection from the microfluidic die.

The correct firing energy for a microfluidic die may be difficult to ascertain to the required degree of accuracy due to several factors, including uncertainties introduced by manufacturing variation in the microfluidic die, fluid composition properties, and driving electronics. For example, the impedance of the heater and of the field effect transistor (controlling flow of current to the heater) may not be precisely known due to variation in process for applying metal to the microfluidic die substrate. The power supply used to supply current to the heater may have an uncertainty in its output voltage, leading to uncertainty in the power available at the heater.

In the following procedure, it is to be understood that the thermal actuators in the microfluidic die are to be operated at a fixed voltage, and thus the energy delivered to the thermal-actuators is proportional to the pulse width applied to the thermal actuator. Therefore, when the procedure determines a firing pulse width that is the minimum required to eject a droplet of fluid composition, that pulse width corresponds to the minimum-required actuation energy.

Figure 11:
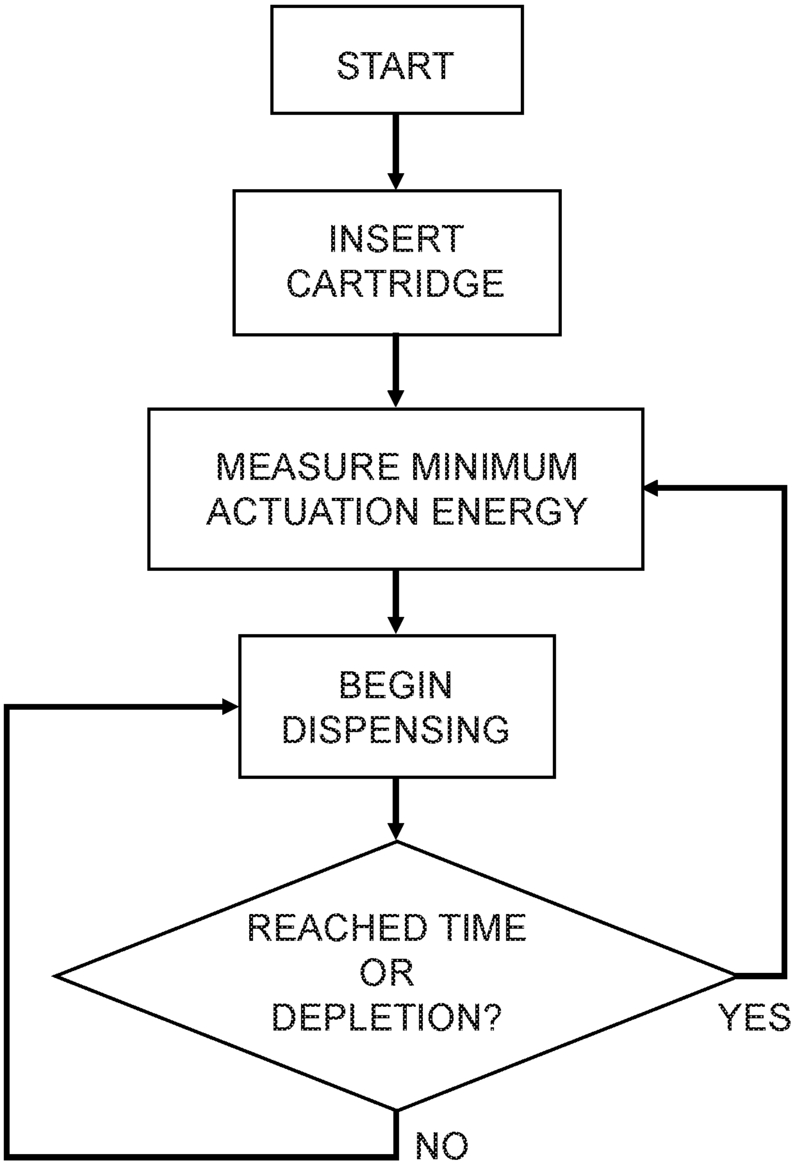
FIG. 11 is a flow chart illustrating the method for atomizing a fluid composition by repeatedly measuring the minimum-required actuation energy.
Figure 12:
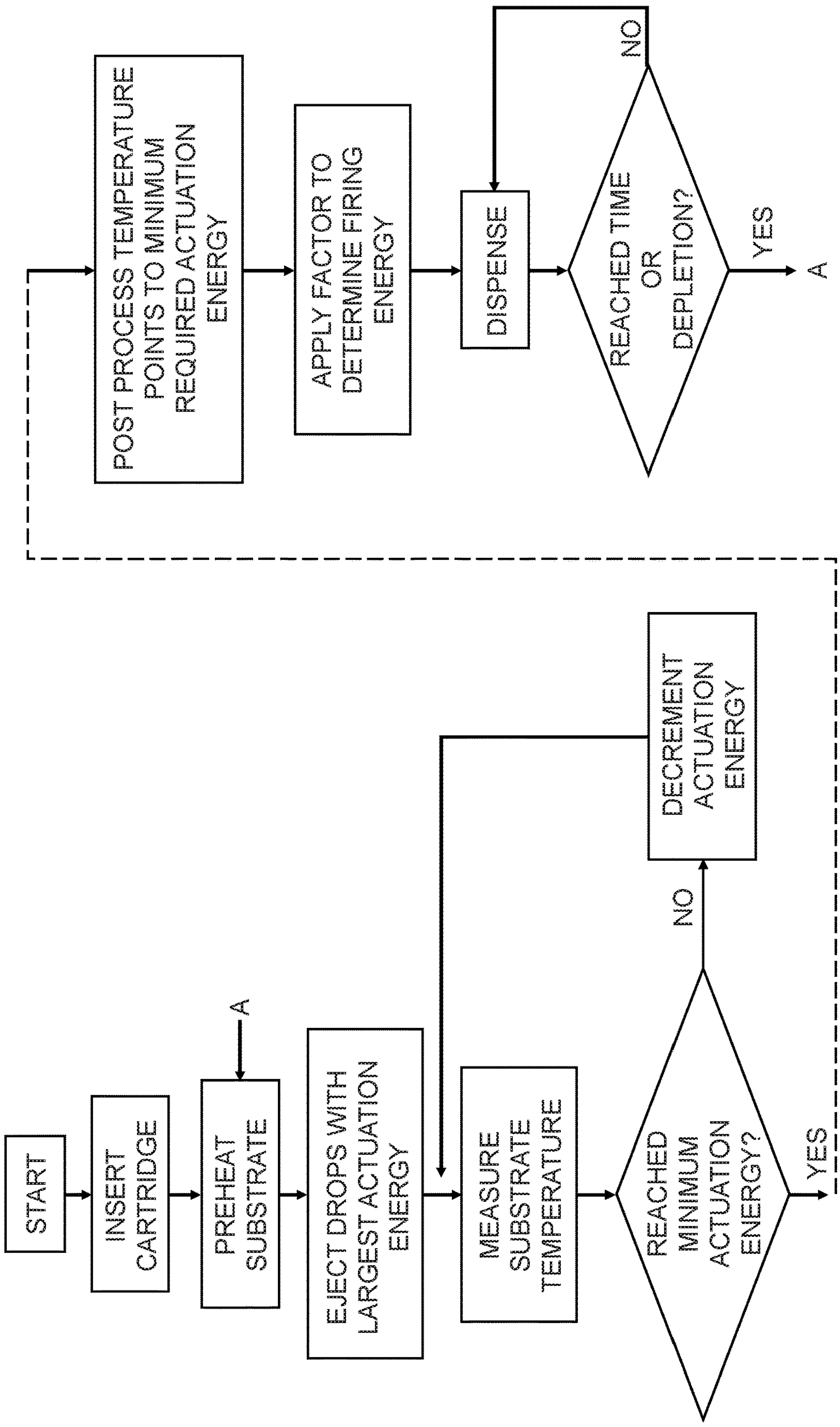
FIG. 12 is a flow chart illustrating the method of atomizing a fluid composition by repeatedly determining the firing energy based on the minimum-required actuation energy.

The process for determining the required minimum-required actuation energy generally follows the procedure described in U.S. Patent Publication No. US2010/0165029A1, entitled "Printhead nucleation detection using thermal response". With reference to FIGS. 11 and 12, in this procedure, firing pulses are delivered to the ink jet die in two modes. The first mode provides firing pulses known to be too short to initiate bubble nucleation in the chamber of the microfluidic die. At the same time, the firing frequency is high enough to provide energy to the substrate of the microfluidic die, which is observed as a rise in temperature of the substrate. In the case of a micro-thermal actuator, the microfluidic die can be heated to a predetermined temperature, which is usually 5-10° C. above the normal operating temperature of the microfluidic die. In the second mode, firing pulse width and firing frequency are coordinated in a way such that the electrical power delivered to the microfluidic die is constant throughout the mode. During the second mode, the firing pulse width is adjusted periodically, starting from a value known to be substantially above the minimum-required actuation energy required for droplet ejection, and proceeding to shorter values, ending at a value known to be too short to eject a droplet. Since the electrical power delivered to the microfluidic die is constant throughout the duration of the second mode, the temperature change of the microfluidic die substrate is influenced by the cooling effect of the fluid as it leaves the chamber (or lack of cooling when no liquid is being ejected). In this way, the point in time (and thus the corresponding firing pulse width) can be identified where liquid composition ceases firing from the chamber through the observation of substrate temperature vs time.

Figure 9:
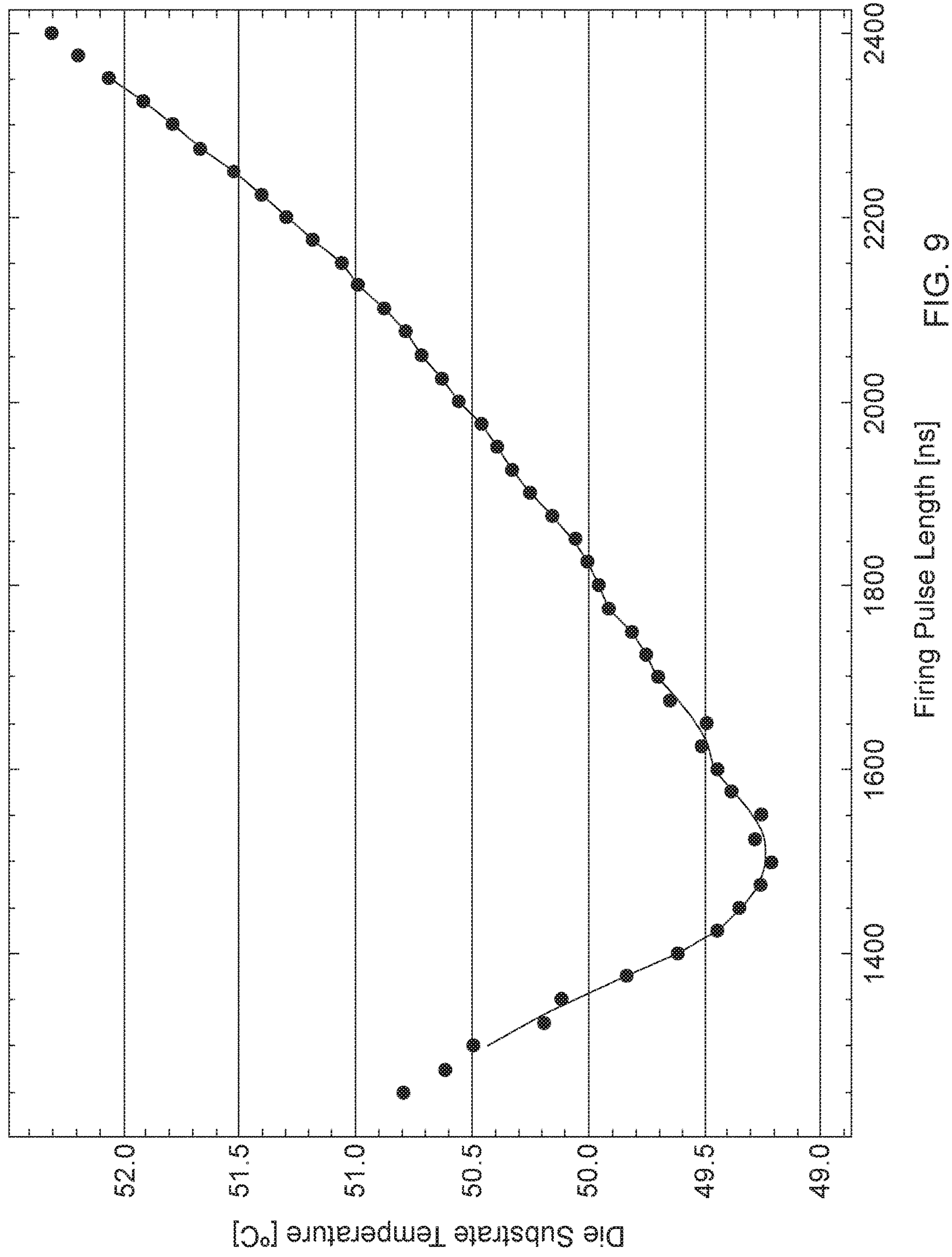
FIG. 9 is a plot of temperature of the microfluidic die substrate versus firing pulse width.
Figure 10:
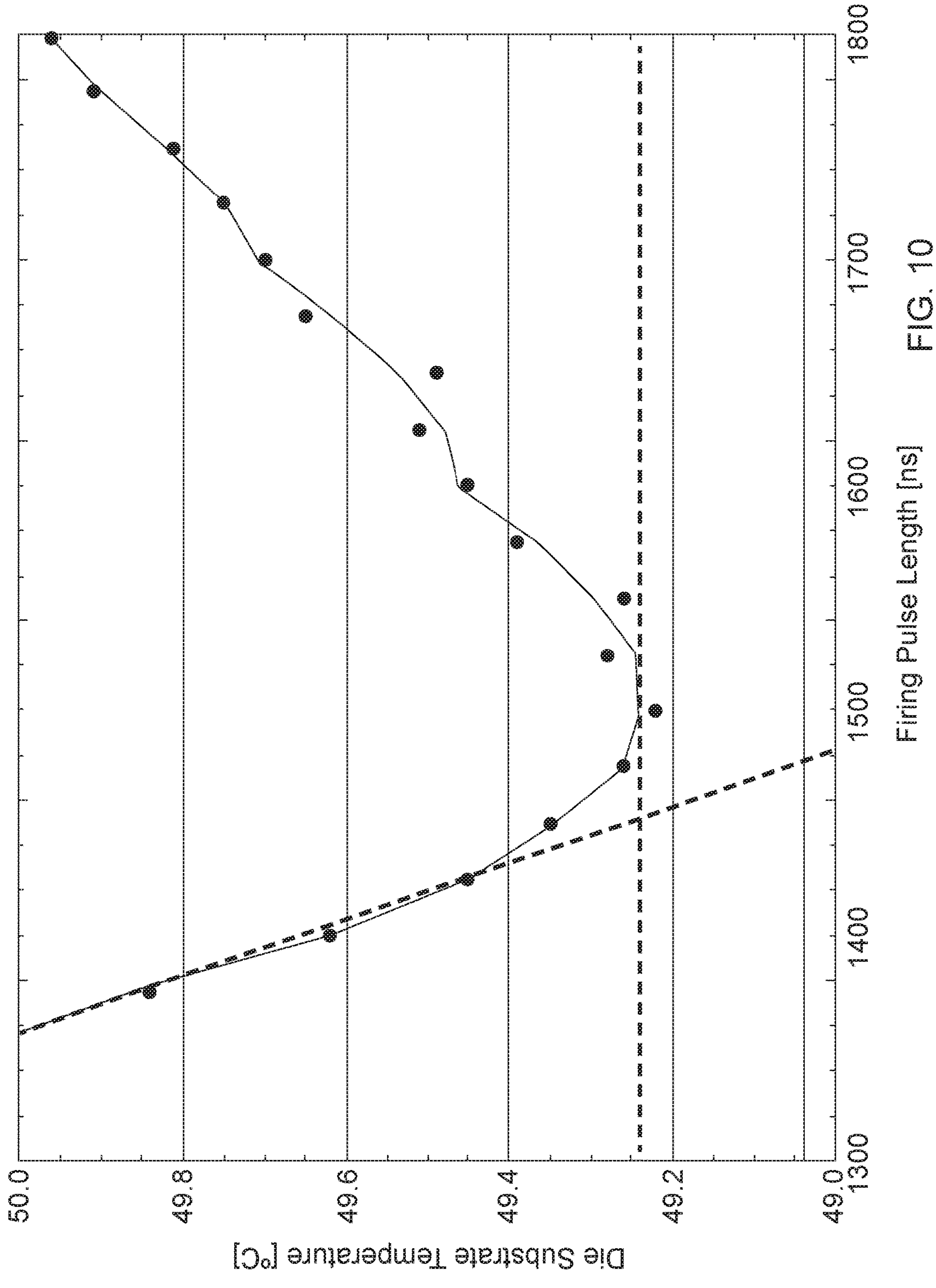
FIG. 10 is a plot of temperature of the microfluidic die substrate versus firing pulse width, used to determine the minimum-required actuation energy for a microfluidic die.

FIG. 9 shows a typical temperature vs. firing pulse width plot of the second mode. Note that in this plot, data points are collected from right to left, as the firing pulse width is varied from longer values to shorter values. The microfluidic die substrate temperature starts initially at the preheat temperature. In this typical case, the temperature decreases, as a liquid cooling from the ejected drops carries heat away from the microfluidic die. As the firing pulse width is reduced, at some point the pulse width becomes too short to sustain droplet ejection, and the liquid cooling ceases. Since the applied power in the second mode of operation is maintained constant, the microfluidic die temperature increases. The local minimum of temperature in this area can be used to infer the minimum-required actuation energy In order to arrive at an unambiguous value for the minimum-required actuation energy the following signal processing is applied to the collected data points. A sloped line is fitted to the temperature points collected after drop firing ceases, and a horizontal line is located at the minimum temperature measured. The intersection of these two lines yields a value of firing pulse width which is inferred to be the minimum-required actuation energy. FIG. 10 illustrates the geometric construction which yields the minimum-required actuation energy estimate.

The sloped line may be determined by a number of methods. The method used here requires determining the slope of temperature with respect to firing pulse width for each data point. An appropriate filtering and derivative estimating algorithm may be used, for example a second degree, five-point, first derivative estimate using Savitsky-Golay polynomials. The point having the maximum slope is used to construct the sloped line, where the sloped line passes through that point, and having that point's slope.

After determining the minimum-required actuation energy, a factor can be applied to obtain the operating firing energy. For example, if the minimum firing energy is determined to be 4 μJ, the ink jet ejector may be operated with a firing energy of 1.2×4 μJ, or 4.8 μJ. The proper choice of excess energy factor ensures that the ejector operates robustly, where small variations in operating conditions such as temperature and voltage have a negligible effect on the performance of the ejector.

Once the firing energy is determined, the controller can instruct the microfluidic die to apply the minimum-required actuation energy or the firing energy to the actuators to jet the fluid composition from the nozzles of the microfluidic die.

In the procedure for determining the minimum-required actuation energy, an alternative means may be employed to replace or supplement the heat provided to the microfluidic die substrate by the fluid ejection actuators. For example, dedicated substrate heaters may be used to heat the substrate in the first mode, and to supplement the thermal energy provided by the actuators in the second mode. This alternative procedure may be used for a micro-mechanical actuator, such as a piezo actuator.

Due to the nature of some fluid compositions, it may be necessary to periodically measure the minimum-required actuation energy throughout the life of the cartridge between periods of dispensing the fluid composition from the microfluidic die. This may be made necessary through the buildup of components of the fluid composition on the heater surface, heat-generated reactants that deposit on ejector surfaces, changes brought about in the composition due to age or environmental factors, or buildup of materials in the vicinity of the nozzle. Fluid compositions having a high number of components may cause one or more of these results. For example, fluid compositions having at least 10 components, or at least 15 components, or at least 20 components, or at least 40 components may benefit more from periodic measurement of the minimum-required actuation energy. A fluid composition having a high number of components, particularly where the components encompass a wide range of vapor pressures, may especially benefit from periodic measurement of the minimum-required actuation energy. Example vapor pressure ranges may include $1.3\times10^{-7}$ Pascals (Pa) to 2000 PA at 20° C. and having a ratio of highest to lowest vapor pressure of at least $1.5\times10^{10}$. The same may also be true for a fluid composition comprising a variety of different classes of materials. For example, the fluid composition may comprise 3, 4, 5, 6, or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

Where the fluid composition comprises many components or classes of materials and where the components or classes of materials are a combination of high volatility and low volatility materials, evaporation of the high volatility components may result in residual which is highly viscous or solid. This residue may impede the functioning of the microfluidic die through deposition on various microfluidic die surfaces. When the fluid composition comprises compounds that may react at high temperatures, this may result in products of reaction that similarly impede the function of the microfluidic die.

The minimum-required actuation energy measurement period may be based strictly on elapsed time, or may be coordinated with the depletion of the fluid composition. Preferably, the minimum-required actuation energy is assessed initially for a new microfluidic cartridge, and then after every 10% of mass dispensed. The mass dispensed is estimated using the accumulated number of firings and the expected average mass dispensed per firing. The expected average mass dispensed per firing is encoded in the memory of the microfluidic cartridge. The final firing energy is determined as the product of a factor (also encoded in the memory of the cartridge) and the measured minimum-required actuation energy.

Fluid Composition

To operate satisfactorily in a microfluidic delivery system, many characteristics of a fluid composition are taken into consideration. Some factors include formulating fluid compositions with viscosities that are optimal to emit from the microfluidic delivery die, formulating fluid compositions with limited amounts or no suspended solids that would clog the microfluidic delivery die, formulating fluid compositions to be sufficiently stable to not dry and clog the microfluidic delivery member, formulating fluid compositions that are not flammable, etc. For adequate dispensing from a microfluidic die, proper atomization and effective delivery of an air freshening or malodor reducing composition may be considered in designing a fluid composition.

The fluid composition may exhibit a viscosity of less than 20 centipoise ("cps"), alternatively less than 18 cps, alternatively less than 16 cps, alternatively from about 3 cps to about 16 cps, alternatively about 4 cps to about 12 cps. The fluid composition may have a surface tension below about 35, alternatively from about 20 to about 30 dynes per centimeter. Viscosity is reported in cps, as determined using an Anton Paar Kinematic SVM 3000 series Viscometer or equivalent measurement device capable of accurately measuring expected viscosity range of fluid at room temperature. This may also be a combination of instruments such as a Bohlin CVO Rheometer System in conjunction with a high sensitivity double gap geometry.

The fluid composition may be substantially free of suspended solids or solid particles existing in a mixture wherein particulate matter is dispersed within a liquid matrix. The fluid composition may have less than 20 wt. % of suspended solids, alternatively less than 15 wt. % of suspended solids, alternatively less than 10 wt. % of suspends, alternatively less than 5 wt. % of suspended solids, alternatively less than 4 wt. % of suspended solids, alternatively less than 3 wt. % of suspended solids, alternatively less than 2 wt. % of suspended solids, alternatively less than 1 wt. % of suspended solids, alternatively less than 0.5 wt. % of suspended solids, or free of suspended solids.

Suspended solids are distinguishable from dissolved solids that are characteristic of some perfume materials.

It is contemplated that the fluid composition may comprise other volatile materials in addition to or in substitution for the perfume mixture including, but not limited to, volatile dyes; compositions that function as insecticides; essential oils or materials that acts to condition, modify, or otherwise modify the environment (e.g. to assist with sleep, wake, respiratory health, and like conditions); deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

Perfume Mixture

The fluid composition may comprise a perfume mixture. If present, the perfume mixture may be present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%.

The perfume mixture may contain one or more perfume raw materials. The raw perfume materials may be selected based on the material's boiling point ("B.P."). The B.P. referred to herein is the boiling point under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969. Where the experimentally measured boiling point of individual components is not available, the value may be estimated by the boiling point PhysChem model available from ACD/Labs (Toronto, Ontario, Canada).

The perfume mixture may have a mole-weighted average log of the octanol-water partitioning coefficient ("ClogP") of less than about 3.5, alternatively less than about 2.9, alternatively less than about 2.5, alternatively less than about 2.0. Where the experimentally measured log P of individual components is not available, the value may be estimated by the boiling point PhysChem model available from ACD/Labs (Toronto, Ontario, Canada).

It may be useful to optimize the fluid composition and/or perfume mixture of the fluid composition for critical pressure and critical temperature. The critical pressure may be optimized for bubble-formation energetics and critical temperature for kogation propensity.

The perfume mixture may have a mol-weighted average B.P. of less than 250° C., alternatively less than 225° C., alternatively less than 200° C., alternatively less than about 150° C., or alternatively about 150° C. to about 250° C.

Alternatively, about 3 wt. % to about 25 wt. % of the perfume mixture may have a mol-weighted average B.P. of less than 200° C., alternatively about 5 wt. % to about 25 wt. % of the perfume mixture has a mol-weighted average B.P. of less than 200° C.

For purposes of the present disclosure, the perfume mixture boiling point is determined by the mole-weighted average boiling point of the individual perfume raw materials making up said perfume mixture. Where the boiling point of the individual perfume materials is not known from published experimental data, it is determined by the boiling point PhysChem model available from ACD/Labs.

Table 1 lists some non-limiting, exemplary individual perfume materials suitable for the perfume mixture.

TABLE 1

| CAS Number | Perfume Raw Material Name | B.P.(° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 40-82-6 | Eucalyptol | 175 |
| 141-78-6 | Ethyl acetate | 77 |

Table 2 shows an exemplary perfume mixture having a total molar weighted average B.P. ("mol-weighted average boiling point") less than 200° C. In calculating the mole-weighted average boiling point, the boiling point of perfume raw materials that may be difficult to determine, may be neglected if they comprise less than 15% by weight of the total perfume mixture, as exemplified in Table 2.

TABLE 2

| CAS Number | Perfume Raw Material Name | Wt. % | Molecular Weight | Mol % | B.P. (° C.) |
|---|---|---|---|---|---|
| 123-68-2 | Allyl Caproate | 2.50 | 156.2 | 2.6 | 185 |
| 140-11-4 | Benzyl Acetate | 3.00 | 150.2 | 3.3 | 214 |
| 928-96-1 | Beta Gamma Hexenol | 9.00 | 100.2 | 14.8 | 157 |
| 18479-58-8 | Dihydro Myrcenol | 5.00 | 156.3 | 5.3 | 198 |
| 39255-32-8 | Ethyl 2 Methyl Pentanoate | 9.00 | 144.2 | 10.3 | 157 |
| 77-83-8 | Ethyl Methyl Phenyl Glycidate | 2.00 | 206.2 | 1.6 | 260 |
| 7452-79-1 | Ethyl-2-Methyl Butyrate | 8.00 | 130.2 | 10.1 | 132 |
| 142-92-7 | Hexyl Acetate | 12.50 | 144.2 | 14.3 | 146 |
| 68514-75-0 | Orange Phase Oil 25X1.18%-Low Cit. 14638 | 10.00 | mixture | neglected | 177 |
| 93-58-3 | Methyl Benzoate | 0.50 | 136.1 | 0.6 | 200 |
| 104-93-8 | Para Cresyl Methyl Ether | 0.20 | 122.2 | 0.3 | 176 |
| 1191-16-8 | Prenyl Acetate | 8.00 | 128.2 | 10.3 | 145 |
| 88-41-5 | Verdox | 3.00 | 198.3 | 2.5 | 223 |
| 58430-94-7 | Iso Nonyl Acetate | 27.30 | 186.3 | 24.1 | 225 |
| | TOTAL: | 100.00 | | 100.0 | |
| | Mol-weighted average B.P. | | | | 176.4 |

Solubilizing Materials

The compositions of the present disclosure may contain one or more solubilizing materials that are liquid at 20° C., where the solubilizing materials have a Hansen hydrogen-bonding parameter of greater than 9; a Hansen polarity parameter of greater than 5; and a vapor pressure of less than 267 Pa, measured at 25° C. Without wishing to be bound by theory, it is believed that the solubilizing materials regulate evaporation of any fluid composition deposited on the surface of the thermally-activated microfluidic die, thus limiting the mass transfer rate of liquid and transition of unstable materials in fluid to solid and preventing gel formation or solidification and blocking of the nozzles.

In the context of the present disclosure, the Hansen solubility parameter is defined as the square root of the cohesive energy density delta=$(E/V)^{1/2}$, where V is the molar volume and E is the energy of vaporization. The basis of the Hansen solubility parameter (HSP) is that the total energy of vaporization of a liquid consists of several individual parts. Hansen has defined three types of contributions to the energy of vaporization, namely: dispersive ($\delta_d$), polar ($\delta_p$), and hydrogen bonding ($\delta_h$). Each parameter, $\delta_d$, $\delta_p$, and $\delta_h$, is generally measured in $MPa^{0.5}$.

The hydrogen-bonding Hansen Solubility Parameter is based upon the hydrogen bonding cohesive energy contribution to the energy of vaporization. The polar Hansen Solubility Parameter is based upon the polar cohesive energy contribution to the energy of vaporization. The hydrogen-bonding Hansen Solubility Parameter and the polar Hansen Solubility Parameter can either be calculated or predicted using the HSPiP Software, available at the following web address https://www.hansen-solubility.com/HSPiP/. The Sphere algorithm is as described in Hansen, C. M., *Hansen Solubility Parameters: A User's Handbook*, CRC Press, Boca Raton Fla., 2007. The Y-MB methodology was developed by Dr Hiroshi Yamamoto of Asahi Glass Corporation.

The HSPiP Software relies on a database with a limited number of materials. If HSPiP database does not have the material of interest, the following equations can be used to calculate the Hansen solubility parameters:

$$Ra^2=4(\delta D1-\delta D2)^2+(\delta P1-\delta P2)^2+(\delta H1-\delta H2)^2$$

RED Ra/R0

More information on the calculations can be found at https://www.hansen-solubility.com/HSP-science/basics.php.

The compositions of the present disclosure may comprise or consist essentially of greater than 1 wt. %, or greater than 5 wt. %, or greater than 8 wt. %, or greater than 10 wt. %, or greater than 12 wt. %, or greater than 15 wt. %, or greater than 18 wt. %, or greater than 20 wt. % of a solubilizer having a Hansen hydrogen-bonding parameter of greater than 9 $MPa^{0.5}$, a Hansen polarity parameter of greater than 5 $MPa^{0.5}$, and a vapor pressure of less than 267 Pascals (Pa) measured at 25° C. The Hansen hydrogen-bonding parameter may be greater than 9 $MPa^{0.5}$, or greater than 10 $MPa^{0.5}$, or greater than 12 $MPa^{0.5}$, or greater than 15 $MPa^{0.5}$. The Hansen polarity parameter may be greater than 5 $MPa^{0.5}$, or greater than 6 $MPa^{0.5}$, or greater than 7 $MPa^{5}$, or greater than 8 $MPa^{0.5}$. The vapor pressure may be less than 267 Pa, preferably less than 137 Pa, preferably less than 67 Pa, preferably less than 34 Pa, more preferably less than 14 Pa, and more preferably less than 1.5 Pa, measured at 25° C.

A solubilizer having a Hansen hydrogen-bonding parameter of greater than 9 $MPa^{0.5}$, a Hansen polarity parameter of greater than 5 $MPa^{0.5}$, and a vapor pressure of less than 267 Pa measured at 25° C., may be selected from the group consisting of: 3-hydroxybutan-2-one (Acetyl Methyl Carbinol, CAS No. 513-86-0); 1-hydroxypropan-2-one (ACETOL, CAS No. 116-09-6); N,N-Dimethylacetamide (CAS No. 127-19-5); 3-hydroxypentan-2-one (acetyl ethyl carbinol, CAS No. 3142-66-3); isobutyric acid (Isobutyric acid, ≥99%. FCC, CAS No. 79-31-2); 5-HEXENOL (CAS No. 821-41-0); 4-methylpentan-1-ol (4-METHYL-1-PENTANOL, CAS No. 626-89-1); ethyl 2-hydroxypropanoate (Ethyl Lactate, CAS No. 97-64-3); dimethyl malonate (CAS No. 108-59-8); (E)-hex-3-en-1-ol (3-hexen-1-ol, CAS No. 544-12-7); (E)-hex-3-en-1-ol (trans-3-HEXEN-1-OL, CAS No. 928-97-2); heptan-3-ol (3-Heptanol, ≥98%, CAS No. 589-82-2); 2-mercaptoethan-1-ol (2-HYDROXYETHANETHIOL, CAS No. 60-24-2) furan-2-ylmethanol (FURFURYL ALCOHOL, CAS No. 98-00-0); 2-oxopropanoic acid (PYRUVIC ACID BRI, CAS No. 127-17-3); 1,5diaminopentane (CAS No. 462-94-2); hexan-1-ol (Hexanol, CAS No. 111-27-3); (E)-hex-4-en-1-ol (TRANS-4-HEXENOL, CAS No. 6126-50-7); heptan-2-ol (2-Heptanol, ≥97%, CAS No. 543-49-7); (E)-hex-2-en-1-ol (TRANS-2-HEXENOL, CAS No. 2305-21-7); (Z)-hex-2-en-1-ol (cis- 2-HEXEN-1-OL, CAS No. 928-94-9); I-AMINO-2-PROPANOL (CAS No. 78-96-6); methyl furan-2-carboxylate (METHYL 2-FUROATE, CAS No. 611-13-2); 1-hydroxybutan-2-one (1-HYDROXY-2-BUTANONE, CAS No. 5077-67-8); 3-(methylthio)hexan-1-ol (3-Methylthio)-1-hexanol, ≥97%, CAS No. 51755-66-9); Methyl sulfoxide, ≥99% (CAS No. 67-68-5); 3-mercaptobutan-2-ol (2-Mercapto-3-butanol, mixture of isomers, ≥97%, FG, CAS No. 37887-04-0); 3-methyl-2-oxobutanoic acid (dimethyl pyruvic acid, CAS No. 759-05-7); 3-methoxy-3-methylbutan-1-ol (3-Methoxy-3-Methyl-1-Butanol, CAS No. 56539-66-3); (5-methylfuran-2-yl)methanol (5-methyl furfuryl alcohol, CAS No. 3857-25-8); 2,4-Dimethyl-2-pentenoic acid (CAS No. 21016-46-6); 2-methylbutanoic acid (METHYL-2-BUTYRIC ACID NAT, CAS No. 116-53-0); 2-butoxyethan-1-ol (2-Butoxyethanol, CAS No. 111-76-2); 4-hydroxy-4-methylpentan-2-one (4-Hydroxy-4-methyl-2-pentanone, CAS No. 123-42-2); ethyl 2-hydroxy-2-methylbutanoate (ethyl 2-hydroxy-2-methyl butyrate, CAS No. 77-70-3); 2-(methylthio)ethan-1-ol (2-(METHYLTHIO)ETHANOL, CAS No. 5271-38-5); 2-oxobutanoic acid (2-Oxobutyric acid, ≥97%, 600-18-0); 3-METHYLCYCLOHEXANOL (CAS No. 591-23-1); 2-METHYLCYCLOHEXANOL (CAS No. 583-59-5); 3-(ethylthio)propan-1-ol (3-Ethylthiopropanol, CAS No. 18721-61-4); propyl 2-hydroxypropanoate (PROPYL LACTATE, CAS No. 616-09-1); (E)-hept-4-en-1-ol (cis-4-HEPTEN-I-OL, CAS No. 6191-71-5); thiophene-2-carbaldehyde (2-THIOPHENECARBOXALDEHYDE, CAS No. 98-03-3); ethyl 3-hydroxybutanoate (Ethyl-3-Hydroxy Butyrate, CAS No. 5405-41-4); 2-hydroxybenzaldehyde (Salicylaldehyde, ≥98%, CAS No. 90-02-8); (tetrahydrofuran-2-yl)methanol (Tetrahydrofurfuryl alcohol, ≥98%, CAS No. 97-99-4); heptan-1-ol (Heptyl alcohol, ≥97%, FCC, CAS No. 111-70-6); (2E,4Z)-hexa-2,4-dien-1-ol (2,4-HEXADIEN-1-OL (SORBIC ALCOHOL), CAS No. 111-28-4); (2E,4Z)-hexa-2,4-dien-1-ol (trans, trans-2,4-Hexadien-1-ol, ≥97%, CAS No. 17102-64-6); furan-2(5H)-one (2(5H)-furanone, CAS No. 497-23-4); 2,3-BUTANEDIOL (CAS No. 513-85-9); methyl 2-hydroxy-4-methylpentanoate (methyl 2-hydroxy-4-methyl valerate, CAS No. 40348-72-9); 2-(ethylthio)ethan-1-ol (ethyl 2-hydroxyethyl sulfide, CAS No. 110-77-0); propane-1,2-diol (1,2 PROPYLENE GLYCOL, CAS No. 57-55-6); propane-1,2-diol (PROPYLENE GLYCOL, CAS No. 57-55-6); formamide (CAS No. 75-12-7); 2-ethylbutanoic acid (2-Ethylbutyric acid, ≥98%, FCC, CAS No. 88-09-5); 2-methylpentanoic acid (2-METHYL PENANOIC ACID FCC, CAS No. 97-61-0); 2-methoxyphenol (Guaiacol, natural, ≥98%, FG, CAS No. 90-05-1); (S)-3-(ethylthio)butan-1-ol (3-(ethyl thio) butanol, CAS No. 117013-33-9); (S)-3-hydroxyoctan-2-one (3-hydroxy-2-octanone, CAS No. 37160-77-3); 1-(thiophen-2-yl)ethan-1-one (2-ACETYLTHIOPHENE, CAS No. 88-15-3); 4-(methylthio)butan-1-ol (4-Methylthiobutanol, CAS No. 20582-85-8); 2-(methylthio)phenol (O-(METHYLTHIO)PHENOL, CAS No. 1073-29-6); phenylmethanol (BENZYL ALCOHOL, CAS No. 100-51-6); 3-(methylthio)propan-1-ol (3-(Methylthio)-1-propanol, ≥98%, FG, CAS No. 505-10-2); butyl 2-hydroxypropanoate (Butyl (S)-(−)-lactate, ≥97%, CAS No. 34451-19-9); butyl 2-hydroxypropanoate (BUTYL LACTATE, CAS No. 138-22-7); 3-mercapto-3-methylbutan-1-ol (3-MERCAPTO-3-METHYL-1-BUTANOL, CAS No. 34300-94-2); 3-methylpentanoic acid (3-METHYL PENTANOIC ACID, CAS No. 105-43-1); butyramide (BUTYRAMIDE, CAS No. 541-35-5); (E)-2-methylpent-3-enoic acid (2-METHYL-3-PENTENOIC ACID, CAS No. 37674-63-8); 1-phenylethan-1-ol (α-Methylbenzyl alcohol, ≥99%, FCC, CAS No. 98-85-1); 2,4-dimethylphenol (CAS No. 105-67-9); 1-(2,4-dimethyl-1,3-dioxolan-2-yl)ethan-1-ol (acetoin propylene glycol acetal, CAS No. 94089-23-3); 2-mercapto-2-methylpentan-1-ol (Tropicol 0.1% IPM, CAS No. 258823-39-1); 2-(2-methoxyethoxy)ethan-1-ol (METHYL CARBITOL, CAS No. 111-77-3); octan-1-ol (OCTYL ALCOHOL, CAS No. 111-87-5); Ethyl (±)-2-hydroxycaproate, ≥97% (CAS No. 52089-55-1); (E)-pent-2-enoic acid (2-PENTENOIC ACID, CAS No. 13991-37-2); 2-mercaptopropanoic acid (2-Mercaptopropionic acid, ≥95%, CAS No. 79-42-5); ethyl (2R,3S)-2-hydroxy-3-methylpentanoate ((+/−)-ETHYL-2-HYDROXY-3-METHYL-VALERATE, CAS No. 24323-38-4); 2-methylpentane-2,4-diol (HEXYLENE GLYCOL, CAS No. 107-41-5); (S)-4-mercapto-4-methylpentan-2-ol (4-mercapto-4-methyl-2-pentanol, CAS No. 31539-84-1); 1-(p-tolyl)ethan-1-ol (a,p-DIMETHYLBENZYL ALCOHOL, CAS No. 536-50-5); (E)-hex-3-enoic acid (trans-3-Hexenoic acid, ≥98%, CAS No. 1577-18-0); (Z)-hex-3-enoic acid (cis-3-HEXENOIC ACID BRI (NATURAL), CAS No. 1775-43-5); 2-methoxy-4-methylphenol (2-Methoxy-4-methylphenol, ≥98%, FG, CAS No. 93-51-6); 2-(2-ethoxyethoxy)ethan-1-ol (DIETHYLENE GLYCOL MONO ETHYLETHER, CAS No. 111-90-0); isopentyl 2-hydroxypropanoate (ISOAMYL LACTATE, CAS No. 19329-89-6); methyl 2-hydroxybenzoate (METHYL SALICYLATE USP, CAS No. 119-36-8); 1-(2-methoxypropoxy)propan-2-ol (DIPROPYLENE GLYCOL METHYL ETHER, CAS No. 34590-94-8); heptanoic acid (heptanoic acid, CAS No. 111-14-8); DIMETHYL SULFONE(CAS No. 67-71-0); (Z)-2-methylpent-2-enoic acid (Strawberiff, CAS No. 3142-72-1); (E)-4-methylpent-2-enoic acid (4-METHYL-2-PENTENOIC ACID, CAS No. 10321-71-8); 2,4-DIMETHYL-2-PENTENOIC ACID (CAS No. 66634-97-7); 2-(ethoxymethyl)phenol (alpha-ethoxy-ortho-cresol, CAS No. 20920-83-6); 3-mercaptopropanoic acid (3-MERCAPTOPROPIONIC ACID, CAS No. 107-96-0); ethyl 2-hydroxybenzoate (ETHYL SALICYLATE, CAS No. 118-61-6); mercaptoacetic acid (CAS No. 68-11-1); 2-Pyrrolidone (CAS No. 616-45-5); 3-phenylpropan-1-ol (PHENYL PROPYL ALCOHOL, CAS No. 122-97-4); hexyl 2-hydroxypropanoate (HEXYL LACTATE, CAS No. 20279-51-0); 1-(2-aminophenyl)ethan-1-one (2-AMINOACETOPHENONE, CAS No. 551-93-9); methyl 3-hydroxyhexanoate (Methyl 3-hydroxyhexanoate, ≥97%, FG, CAS No. 21188-58-9); 3-methoxyphenol (3-METHOXYPHENOL, CAS No. 150-19-6); 2-methoxy-4-vinylphenol (2-Methoxy-4-vinylphenol, ≥98%, CAS No. 7786-61-0); 4-ethyl-2-methoxyphenol (4-Ethylguaiacol, ≥98%, FCC, FG, CAS No. 2785-89-9); 2-(o-tolyl)ethan-1-ol (Peomosa, CAS No. 19819-98-8); 2-(m-tolyl)ethan-1-ol (3-Methylphenethyl alcohol, CAS No. 1875-89-4); 3-(hydroxymethyl)heptan-2-one (3-octanon-1-ol, CAS No. 65405-68-7); 2-phenoxyethan-1-ol (2-PHENOXYETHANOL, CAS No. 122-99-6); lactic acid (CAS No. 50-21-5); 2-allyl-6-methoxyphenol (ortho-eugenol, CAS No. 579-60-2); 5-ethyl-4-hydroxy-2-methylfuran-3(2H)-one (2-Ethyl-4-hydroxy-5-methyl-3(2H)furanone, 20% in PG, CAS No. 27538-09-6); 2-ethyl-4-hydroxy-5-methylfuran-3(2H)-one (Homofuranol Pure 100% neat, CAS No. 27538-09-6); (Z)-oct-5-enoic acid ((Z)-5-octenoic acid, CAS No. 41653-97-8); 4-oxopentanoic acid (Levulinic acid, ≥97%, FG, CAS No. 123-76-2); 4-allyl-2-methoxyphenol (EUGENOL, CAS No. 97-53-0); 3-(methylthio)propanoic acid (3-METHYLTHIOPROPIONIC ACID, CAS No. 646-01-5); (4-methoxyphenyl)methanol (Anisyl Alcohol, CAS No. 105-13-5); 3-hydroxypropane-1,2-diyl diacetate (Diacetin, CAS No. 25395-31-7); 2-methoxy-4-propylphenol (DIHYDRO EUGENOL, CAS No. 2785-87-7); ethyl 3-hydroxyhexanoate (ETHYL 3-HYDROXY HEXANOATE, CAS No. 2305-25-1); 1-((1-propoxypropan-2-yl)oxy)propan-2-ol (Dipropylene glycol n-propyl ether, CAS No. 29911-27-1); (Z)-2-methoxy-4-(prop-1-en-1-yl)phenol ((E)-Isoeugenol, CAS No. 5932-68-3); (E)-2-methoxy-4-(prop-1-en-1-yl)phenol (cis-iso-Eugenol, CAS No. 5912-86-7); (S)-3-(hydroxymethyl)octan-2-one (hydroxymethyl hexyl ethyl ketone, CAS No. 59191-78-5); 2,2'-oxybis(ethan-1-ol) (DIETHYLENE GLYCOL, CAS No. 111-46-6); 4-(methylthio)-2-oxobutanoic acid (4-(methyl thio)-2-oxobutyric acid, CAS No. 583-92-6); N-Methyldiethanolamine (N-Methyldiethanolamine, CAS No. 105-59-9); (E)-hex-3-en-1-yl 2-hydroxypropanoate (cis-3-HEXENYL LACTATE, CAS No. 61931-81-5); 2-ethoxy-4-(methoxymethyl)phenol (Methyl Diantilis®, CAS No. 5595-79-9); 4-(ethoxymethyl)-2-methoxyphenol (VANILLYL ETHYL ETHER, CAS No. 13184-86-6); 2-(4-methylthiazol-5-yl)ethan-1-ol (Sulfurol, CAS No. 137-00-8); (R)-3-hydroxy-4-phenylbutan-2-one (3-hydroxy-4-phenyl-2-butanone, CAS No. 5355-63-5); 3-ethyl-2-hydroxycyclopent-2-en-1-one (ETHYL CYCLOPENTENOLONE PURE, CAS No. 21835-01-8); benzyl 2-hydroxypropanoate (BENZYL LACTATE, CAS No. 2051-96-9); 5-ethyl-2-hydroxy-3-methylcyclopent-2-en-1-one (5-ethyl-3-methyl cyclotene, CAS No. 53263-58-4); 3-ethyl-2-hydroxy-4-methylcyclopent-2-en-1-one (3-ethyl-4-methyl cyclotene, CAS No. 42348-12-9); 2-hydroxy-3,5,5-trimethylcyclohex-2-en-1-one (2-HYDROXY-3,5,5-TRIMETHYL-2-CYCLOHEXENONE, CAS No. 4883-60-7); DIPROPYLENE GLYCOL-N-BUTYL ETHER (CAS No. 29911-28-2); 3-(hydroxymethyl)nonan-2-one (3-(HYDROXYMETHYL)-2-NONANONE, CAS No. 67801-33-6); 3,7-dimethyloctane-1,7-diol (HYDROXYOL, CAS No. 107-74-4); 2-(2-hydroxypropan-2-yl)-5-methylcyclohexan-1-ol (Geranodyle, CAS No. 42822-86-6); propyl 4-hydroxybenzoate (PROPYL-p-HYDROXYBENZOATE, CAS No. 94-13-3); 5-(hydroxymethyl)furan-2-carbaldehyde (5-(Hydroxymethyl)furfural, ≥99%, CAS No. 67-47-0); ethyl 4-hydroxybenzoate (ETHYL-p-HYDROXYBENZOATE, CAS No. 120-47-8); 4-propyl syringol (CAS No. 6766-82-1); 4-allyl-2,6-dimethoxyphenol (4-Allyl-2,6-dimethoxyphenol, ≥90%, CAS No. 6627-88-9); ETHYL-3-HYDROXY OCTANOATE (CAS No. 7367-90-0); diethyl 2,3-dihydroxysuccinate (Diethyl L-tartrate, ≥99%, CAS No. 87-91-2); diethyl 2-hydroxysuccinate (DIETHYL MALATE, CAS No. 626-11-9); triethylene glycol (CAS No. 112-27-6); (2S,3R)-3-(((2S,3R)-3-mercaptobutan-2-yl)thio)butan-2-ol (a-METHYL-b-HYDROXYPROPYL-a-METHYL-b-MERCAPTOPROPYL SULFIDE, CAS No. 54957-02-7); (2-phenyl-1,3-dioxolan-4-yl)methanol (Benzaldehyde glyceryl acetal, CAS No. 1319-88-6); ethyl 3-hydroxy-3-phenylpropanoate (ETHYL-3-HYDROXY-3-PHENYL PROPIONATE, CAS No. 5764-85-2); 1-(heptyloxy)-3-hydroxypropan-2-one (Heptanol gylceryl acetal, CAS No. 72854-42-3); phenethyl 3-hydroxypropanoate (PHENYL ETHYL LACTATE, CAS No. 10138-63-3); 2-methoxy-4-(4-methyl-1,3-dioxolan-2-yl)phenol (VANILLIN PROPYLENE GLYCOL ACETAL, 68527-74-2); 3-hydroxy-4,5-dimethylfuran-2(5H)-one (CARAMEL FURANONE (3% IN TRIACETIN), CAS No. 28664-35-9); 5-ethyl-3-hydroxy-4-methylfuran-2(5H)-one (MAPLE FURANONE (NEAT), CAS No. 698-10-2); 2-ethoxy-4-(4-methyl-1,3-dioxolan-2-yl)phenol (ETHYL VANILLIN PROPYLENE GLYCOL ACETAL, CAS No. 68527-76-4); 2-hydroxy-1,2-diphenylethan-1-one (Benzoin, CAS No. 119-53-9); 3-((2-isopropyl-5-methylcyclohexyl)oxy)propane-1,2-diol (3-1-MENTHOXYPROPANE-1,2-DIOL, CAS No. 87061-04-9); (R)-2-hydroxy-N-(2-hydroxyethyl)propanamide (lactoyl ethanolamine, CAS No. 5422-34-4); 2,3-dihydroxypropyl 5-hydroxydecanoate (glyceryl 5-hydroxydecanoate, CAS No. 26446-31-1); 1-hydroxy-4-methyl-2-pentanone (1-hydroxy-4-methyl-2-pentanone, CAS No. 68113-55-3); 2-(2-hydroxypropoxy)propan-1-ol (dipropylene glycol, CAS No. 25265-71-8); 2-phenylethan-1-ol (Phenyl Ethyl Alcohol, CAS No. 60-12-8); and combinations thereof.

A solubilizer having a Hansen hydrogen-bonding parameter of greater than 9 $MPa^{0.5}$, a Hansen polarity parameter of greater than 5 $MPa^{0.5}$, and a vapor pressure of less than 267 Pa measured at ° C. may be selected from the group consisting of: phenylmethanol; 2-(2-hydroxypropoxy)propan-1-ol; propane-1,2-diol; 1-((1-propoxypropan-2-yl)oxy)propan-2-ol; 1-(2-methoxypropoxy)propan-2-ol; 4-allyl-2-methoxyphenol; 2-phenylethan-1-ol; and combinations thereof.

Secondary Solubilizer

The fluid composition may contain one or more secondary solubilizers in addition to the solubilizing materials disclosed above, such as a polyol (components comprising more than one hydroxyl functionality), a glycol ether, or a polyether. If the secondary solubilizers present in the fluid composition fall within the Hansen solubility parameters and vapor pressure of the solubilizing materials, the secondary solubilizers should be considered in the total weight percentage of the solubilizing materials in the freshening composition.

Exemplary oxygenated solvents comprising polyols include ethylene glycol, diethylene glycol, triethylene glycol, propylene glycol, dipropylene glycol, and/or glycerin. The polyol used in the freshening composition of the present disclosure may be, for example glycerin, ethylene glycol, propylene glycol, dipropylene glycol.

Exemplary oxygenated solvents comprising polyethers are polyethylene glycol, and polypropylene glycol Exemplary oxygenated solvents comprising glycol ethers are propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycol phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. The oxygenated solvent may be ethylene glycol, propylene glycol, or mixtures thereof. The glycol used may be dipropylene glycol.

The oxygenated solvent may be added to the composition at a level of from about 0.01 wt. % to about 50 wt. % by weight of the composition, alternatively from about 0.01 wt. % to about 20 wt. %, by weight of the composition alternatively from about 0.05 wt. % to about 10 wt. %, alternatively from about 0.1 wt. % to about 5 wt. %, by weight of the overall composition.

Water

The fluid composition may comprise water. The fluid composition may comprise water in an amount from about 0.25 wt. % to about 20 wt. % water, alternatively about 0.25 wt. % to about 10 wt. % water, alternatively about 1% to about 5% water, alternatively from about 1% to about 3% water, alternatively from about 1% to about 2% water, by weight of the fluid composition. Without wishing to be bound by theory, it has been found that by formulating the perfume mixture to have a mol-weighted average ClogP of less than about 2.5, water can be incorporated into the fluid composition at a level of about 0.25 wt. % to about 9.5 wt.

%, alternatively about 0.25 wt. % to about 7.0 wt. %, by weight of the overall composition.

Malodor Blockers

The fluid composition may include one or more malodor blockers that dull the sensor of smell to a human, while not unduly interfering with the scent of the fluid compositions. Exemplary malodor blockers may be selected from the group consisting of: 1,1,2,3,3-pentamethyl-1,2,3,5,6,7-hexahydro-4H-inden-4-one (Cashmeran, 33704-61-9); 3a,4,5,6,7,7a-hexahydro-1H-4,7-methanoinden-6-yl acetate Flor (acetate/herbaflorate, CAS No. 5413-60-5); 1-((2-(tert-butyl)cyclohexyl)oxy)butan-2-ol (Ambercore, CAS No. 139504-68-0); 2-(8-isopropyl-6-methylbicyclo[2.2.2]oct-5-en-2-yl)-1,3-dioxolane (Glycolierral/Glycoacetal, CAS No. 68901-32-6); (E)-oxacyclohexadec-13-en-2-one (Habanolide, CAS No. 111879-80-2); (Z)-cyclooct-4-en-1-yl methyl carbonate (Violiff, CAS No. 87731-18-8); 7-methyloctyl acetate (Iso Nonyl Acetate, CAS No. 40379-24-6); ethyl dodecanoate (Ethyl laurate, CAS No. 106-33-2); 4,5-epoxy-4,11,11-trimethyl-8-methylenebicyclo(7.2.0)undecane (Caryophyllene Oxide, CAS No. 1139-30-6); 1,3,4,6,7,8alpha-hexahydro-1,1,5,5-tetramethyl-2H-2,4alpha-methanophthalen-8(5H)-one (Isolongifolanone, CAS No. 23787-90-8); dodecan-1-ol (1-dodecanol, CAS No. 112-53-8); 8,8-dimethyl-3a,4,5,6,7,7a-hexahydro-1H-4,7-methanoinden-6-yl propionate (frutene, CAS No. 76842-49-4); (Z)-non-6-en-1-ol (CIS-6-NONEN-1-OL FCC, CAS No. 35854-86-5); dodecanenitrile (CLONAL, CAS No. 2437-25-4); (E)-dec-4-enal (DECENAL (TRANS-4), CAS No. 65405-70-1); (1-methyl-2-((1,2,2-trimethylbicyclo[3.1.0]hexan-3-yl) methyl)cyclopropyl)methanol (JAVANOL, CAS No. 198404-98-7); (E)-1,1-dimethoxy-3,7-dimethylocta-2,6-diene (CITRAL DIMETHYL ACETAL, CAS No. 7549-37-3); 2,6-di-tert-butyl-4-methylphenol (BHT, CAS No. 128-37-0); oxydibenzene, (Diphenyl oxide, CAS No. 101-84-8); (E)-3,7-dimethylocta-2,6-dien-1-yl palmitate (Hexarose, 3681-73-0); 3-methyl-5-phenylpentan-1-ol (Phenyl hexanol, CAS No. 55066-48-3); 3-(3,3-dimethyl-2,3-dihydro-1H-inden-5-yl)propanal (Hivernal, CAS No. 173445-65-3); 3-(1,1-dimethyl-2,3-dihydro-1H-inden-5-yl)propanal (Hivernal, CAS No. 300371-33-9); 2,2,6,6,7,8,8-heptamethyldecahydro-2H-indeno[4,5-b]furan (Amber x-treme, CAS No. 476332-65-7); (R,Z)-1-(2,6,6-trimethylcyclohex-2-en-1-yl)pent-1-en-3-one (Alpha methyl ionone, CAS No. 127-42-4); 3-(6,6-dimethylbicyclo[3.1.1]hept-2-en-2-yl)-2,2-dimethylpropanal (Pinyl isobutyraldehyde alpha, CAS No. 33885-52-8); (E)-3,7-dimethylocta-1,3,6-triene (Cis-ocimene, CAS No. 3338-55-4); 1-(5,5-dimethylcyclohex-1-en-1-yl)pent-4-en-1-one (Neobutenone alpha, CAS No. 56973-85-4); (E)-cyclohexadec-5-en-1-one (5-cylohexadene-1-one, CAS No. 37609-25-9); 2-isopropyl-5-methylphenol (thymol, CAS No. 89-83-8; and combinations thereof.

The fluid composition may comprise up to 2 wt. % of malodor blockers, or from 0.0001 wt. % to 2 wt. % of malodor blockers, based on the total weight of the fluid composition.

Reactive Aldehydes

The fluid composition may include one or more reactive aldehydes that neutralize malodors in vapor and/or liquid phase via chemical reactions. The reactive aldehydes provide a genuine malodor neutralization and function not merely by covering up or masking odors. A genuine malodor neutralization provides a sensory and analytically measurable (e.g. gas chromatograph) malodor reduction.

Reactive aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase reactive aldehydes to have virtually no negative impact on the desired perfume character of a product. Aldehydes that are partially volatile may be considered a reactive aldehyde as used herein.

Suitable reactive aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The reactive aldehydes may also have a certain boiling point (B.P.) and octanol/water partition coefficient (P). The boiling point referred to herein is measured under normal standard pressure of 760 mmHg. The boiling points of many reactive aldehydes, at standard 760 mm Hg are given in, for example, "Perfume and Flavor Chemicals (Aroma Chemicals)," written and published by Steffen Arctander, 1969.

The octanol/water partition coefficient of a reactive aldehyde is the ratio between its equilibrium concentrations in octanol and in water. The partition coefficients of the reactive aldehydes used in the fluid composition may be more conveniently given in the form of their logarithm to the base 10, log P. The log P values of many reactive aldehydes have been reported. See, e.g., the Pomona92 database, available from Daylight Chemical Information Systems, Inc. (Daylight CIS), Irvine, Calif. However, the log P values are most conveniently calculated by the "CLOGP" program, also available from Daylight CIS. This program also lists experimental log P values when they are available in the Pomona92 database. The "calculated log P" (ClogP) is determined by the fragment approach of Hansch and Leo (cf, A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each reactive aldehyde, and takes into account the numbers and types of atoms, the atom connectivity, and chemical bonding. The ClogP values, which are the most reliable and widely used estimates for this physicochemical property, are alternatively used instead of the experimental log P values in the selection of reactive aldehydes for the fluid composition.

The ClogP values may be defined by four groups and the reactive aldehydes may be selected from one or more of these groups. The first group comprises reactive aldehydes that have a B.P. of about 250° C. or less and ClogP of about 3 or less. The second group comprises reactive aldehydes that have a B.P. of 250° C. or less and ClogP of 3.0 or more. The third group comprises reactive aldehydes that have a B.P. of 250° C. or more and ClogP of 3.0 or less. The fourth group comprises reactive aldehydes that have a B.P. of 250° C. or more and ClogP of 3.0 or more. The fluid composition may comprise any combination of reactive aldehydes from one or more of the ClogP groups.

The fluid composition of the present disclosure may comprise, by total weight of the fluid composition, from about 0% to about 30% of reactive aldehydes from group 1, alternatively about 25%; and/or about 0% to about 10% of reactive aldehydes from group 2, alternatively about 10%; and/or from about 10% to about 30% of reactive aldehydes from group 3, alternatively about 30%; and/or from about 35% to about 60% of reactive aldehydes from group 4, alternatively about 35%. Exemplary reactive aldehydes which may be used in a fluid composition of the present disclosure include, but are not limited to, Adoxal (2,6,10-Trimethyl-9-undecenal), Bourgeonal (4-t-butylbenzenepropionaldehyde), Lilestralis 33 (2-methyl-4-t-butylphenyl) propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-mehtyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), Precylcemone B (1-cyclohexene-1-carboxaldehyde); Pinyl isobutyraldehyde alpha (3-(6,6-dimethylbicyclo[3.1.1]hept-2-en-2-yl)-2,2-dimethylpropanal; and Hivernal (3-(3,3-dimethyl-2,3-dihydro-1H-inden-5-yl)propanal/3-(1,1-dimethyl-2,3-dihydro-1H-inden-5-yl)propanal).

Still other exemplary reactive aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenylpropenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexylcinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

The reactive aldehydes may be present in an amount up to 100%, by weight of the fluid composition, alternatively from 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 1% to about 10%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

The fluid composition of the present disclosure may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present fluid composition contains an acid catalyst and contacts a sulfur-based malodor, the reactive aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 3. Table 3

TABLE 3

| Acid Catalyst | VP (torr) @ 25° C. |
|---|---|
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the fluid composition, one may consider the scent character or the effect on the scent of the fluid composition when selecting an acid catalyst. It may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr. Non-limiting examples of such acid catalyst include 5-methyl thiophene carboxaldehyde with carboxylic acid impurity, succinic acid, or benzoic acid.

The composition may include about 0.05% to about 5%, alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst by weight of the fluid composition. When an acid catalyst is present with a reactive aldehyde, the acid catalyst may increase the efficacy of the reactive aldehyde on malodors in comparison to the malodor efficacy of the reactive aldehyde on its own. For example, 1% reactive aldehyde and 1.5% benzoic acid provides malodor removal benefit equal to or better than 5% reactive aldehyde alone.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of atomizing a fluid composition comprising a perfume mixture from a microfluidic die, the microfluidic die comprising a substrate and a plurality of nozzles, a thermal actuator associated with each nozzle, and wherein the actuator is responsive to a pulse for energizing the fluid composition and jetting the fluid composition through the nozzle, and a thermal sensor for measuring a temperature of the substrate of the microfluidic die, the method comprising:

determining a firing energy to drive the thermal actuators to jet the fluid composition at a first time, wherein the thermal actuators in the microfluidic die are operated at a fixed voltage and determining a firing energy comprises:

heating the microfluidic die to a predetermined temperature by driving the actuators during a first mode with pulses having a pulse width and a starting frequency that does not cause bubble nucleation;

driving the actuators during a second mode with respective pulses having decremented pulse widths and frequencies having incremented frequencies, starting at a pulse width known to cause droplet ejection and ending at a pulse width too short to cause droplet ejection;

processing a temperature change of the microfluidic die during the second mode to determine a minimum-required actuation energy that caused a predetermined temperature change, wherein the minimum-required actuation energy is again determined after every 10% of mass of the fluid composition is dispensed;

applying a factor to the determined minimum-required actuation energy to determine a firing energy; and using the firing energy to drive the thermal actuators to jet the fluid composition;

repeating the step of measuring the firing energy to determine a second firing energy at a second time after the first time; and using the second firing energy to drive the thermal actuators to jet the fluid composition.

2. The method of claim 1, further comprising the step of repeating the measurement of minimum-required actuation energy after subsequent atomization periods.

3. The method of claim 1, wherein the fluid composition comprises at least ten components.

4. The method of claim 3, wherein the ten or more components have a range of vapor pressures encompassing $1.3\times10^{-7}$ Pa to 2000 Pa 20° C. and having a ratio of highest to lowest vapor pressure of at least $1.5\times10^{10}$.

5. The method of claim 1, wherein the fluid composition comprises three or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

6. The method of claim 1, wherein the fluid composition comprises one or more reactive components that form solids.

7. A method of atomizing a fluid composition comprising a perfume mixture from a microfluidic die, the microfluidic die comprising a plurality of nozzles, an actuator associated with each nozzle, and wherein the actuator is responsive to a pulse for energizing the fluid composition and jetting the fluid composition through the nozzle, a means of heating the microfluidic die substrate, and a thermal sensor for measuring microfluidic die substrate temperature, comprising:

measuring a firing energy to drive the actuators to jet the fluid composition at a first time, wherein the thermal actuators in the microfluidic die are operated at a fixed voltage and measuring the firing energy comprises:

a) heating the microfluidic die substrate to a predetermined temperature during a first mode;

b) driving the actuators during a second mode with respective pulses having decremented actuation energy and maintaining a constant power applied to the microfluidic die substrate, starting at an actuation energy known to cause drop ejection and ending at an actuation energy too small to cause drop ejection;

c) processing a temperature change of the microfluidic die during the second mode to determine a minimum-required actuation energy that caused a predetermined temperature change;

d) applying a factor to the determined minimum-required actuation energy to determine a firing energy; and using the firing energy to drive the actuators to jet the fluid composition;

repeating the step of measuring the minimum-required actuation energy to determine a second firing energy at a second time after the first time, after 10% of mass of the fluid composition is dispensed; and using the second firing energy to drive the actuators to jet the fluid composition.

8. The method of claim 7, further comprising the step of repeating the measurement of minimum-required actuation energy after subsequent atomization periods.

9. The method of claim 7, wherein the fluid composition comprises at least ten components.

10. The method of claim 9, wherein the ten or more components have a range of vapor pressures encompassing $1.3\times10^{-7}$ Pa to 2000 Pa at 20° C. and having a ratio of highest to lowest vapor pressure of at least $1.5\times10^{10}$.

11. The method of claim 7, wherein the fluid composition comprises three or more materials selected from the group consisting of: alcohols, aldehydes, acids, ketones, esters, terpenes, amines, sulfides, thiols, ethers, furans, pyrans, pyrroles, pyrrolidine, thiophenes, oxides, epoxides, and combinations thereof.

* * * * *